(12) United States Patent
Holmes et al.

(10) Patent No.: US 7,807,793 B2
(45) Date of Patent: *Oct. 5, 2010

(54) RECOMBINANT IL4 ANTIBODIES USEFUL IN TREATMENT OF IL4 MEDIATED DISORDERS

(75) Inventors: Stephen Dudley Holmes, Epsom (GB); Mitchell Stuart Gross, Wayne, PA (US); Daniel R. Sylvester, Phoenixville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/493,692

(22) Filed: Jul. 26, 2006

(65) Prior Publication Data

US 2006/0263853 A1 Nov. 23, 2006

Related U.S. Application Data

(63) Continuation of application No. 10/723,872, filed on Nov. 26, 2003, now abandoned, which is a continuation of application No. 09/879,461, filed on Jun. 12, 2001, now abandoned, which is a continuation of application No. 09/426,814, filed on Oct. 22, 1999, now abandoned, which is a continuation of application No. 08/612,929, filed as application No. PCT/US94/10308 on Sep. 7, 1994, now abandoned, which is a continuation-in-part of application No. 08/136,783, filed on Oct. 14, 1993, now abandoned, which is a continuation of application No. 08/117,366, filed on Sep. 7, 1993, now abandoned.

(51) Int. Cl.
*C12P 21/08* (2006.01)
*A61K 39/395* (2006.01)

(52) U.S. Cl. .................. 530/387.3; 424/133.1

(58) Field of Classification Search .................. None
See application file for complete search history.

(56) References Cited

U.S. PATENT DOCUMENTS

| 5,041,381 A | 8/1991 | Abrams et al. ......... 435/240.27 |
| 5,108,910 A | 4/1992 | Curtis et al. ............... 435/69.7 |
| 5,597,710 A | 1/1997 | Dalie et al. ................ 435/69.6 |
| 5,705,154 A | 1/1998 | Dalie et al. ............... 424/130.1 |
| 5,770,403 A | 6/1998 | Dalie et al. ................ 435/69.6 |
| 5,914,110 A | 6/1999 | Holmes et al. ........... 424/133.1 |

FOREIGN PATENT DOCUMENTS

| EP | 327 000 | 1/1989 |
| EP | 0 327 283 B1 | 8/1993 |
| JP | 327 725 | 12/1989 |
| JP | 03 187 395 | 8/1991 |
| WO | 89/06975 | * 8/1989 |
| WO | WO90/07861 | 7/1990 |
| WO | WO91/09059 | 6/1991 |
| WO | 9304173 | 3/1993 |
| WO | WO93/17106 | 9/1993 |

OTHER PUBLICATIONS

Rudikoff et al (Proc Natl Acad Sci USA 1982 vol. 79 p. 1979).*
Vajdos et al J. Mol. Biol. 320:415, 2002.*
Abe, et al., "Novel Immunization Protocol and ELISA Screening Methods Used to Obtain and Characterized Monoclonal Antibodies Specific for Human Light Chain Variable-Region Subgroups," *Hybridoma*, 12(4):475-483 (1993).
Chretien, et al. "Development of Polyclonal and Monoclonal Antibodies for Immunoassay and Neutralization of Human Interleukin-4," *Journal of Immunologicals Methods*, 117:67-81 (1989).
Perfetti et al., *Mol Immunol.*, 287:505 (1991).
Harris, TIB Tech 11:42, (1991).
Waldmann, *Science*, 252:1657, (1991).
Weigert et al., *Nature*, 276:785 (1978).
Orlandi, *PNAS*, 86:3833 (1989).
Co et al., *Nature*, 351:501 (1991).
Maggio, *Enzyme-Immunoassay CRC Press Inc.*, p. 167-178 (1980).

* cited by examiner

*Primary Examiner*—Sheela J Huff
(74) *Attorney, Agent, or Firm*—Jonathan M. Dermott; William T. Han

(57) ABSTRACT

Chimeric and humanized IL4 MAbs derived from affinity MAbs, pharmaceutical compositions containing same, and methods of treatment are provided.

6 Claims, 11 Drawing Sheets

FIGURE 1

Murine Antibody 3B9 Light Chain
*Native Signal Sequence* and Variable Region

Nucleotide Sequence SEQ ID NO:1
Amino Acid Sequence SEQ ID NO:2

| | | | | | | | | | | | | |
|---|---|---|---|---|---|---|---|---|---|---|---|---|
| *ATG* | *GAG* | *ACA* | *GAC* | *ACA* | *ATC* | *CTG* | *CTA* | *TGG* | *GTG* | *CTG* | *CTG* | *CTC* | 39 |
| *Met* | *Glu* | *Thr* | *Asp* | *Thr* | *Ile* | *Leu* | *Leu* | *Trp* | *Val* | *Leu* | *Leu* | *Leu* | |
| 1 | | | | 5 | | | | | 10 | | | | |

| *TGG* | *GTT* | *CCA* | *GGC* | *TCC* | *ACT* | *GGT* | GAC | ATT | GTG | CTG | ACC | CAA | 78 |
|---|---|---|---|---|---|---|---|---|---|---|---|---|---|
| *Trp* | *Val* | *Pro* | *Gly* | *Ser* | *Thr* | *Gly* | Asp | Ile | Val | Leu | Thr | Gln | |
| | | 15 | | | | 20 | | | | 25 | | | |

| TCT | CCA | GCT | TCT | TTG | GCT | GTG | TCT | CTA | GGG | CAG | AGG | GCC | 117 |
|---|---|---|---|---|---|---|---|---|---|---|---|---|---|
| Ser | Pro | Ala | Ser | Leu | Ala | Val | Ser | Leu | Gly | Gln | Arg | Ala | |
| | | | 30 | | | | | 35 | | | | | |

| ACC | ATC | TCC | TGC | AAG | GCC | AGC | CAA | AGT | GTT | GAT | TAT | GAT | 156 |
|---|---|---|---|---|---|---|---|---|---|---|---|---|---|
| Thr | Ile | Ser | Cys | <u>Lys</u> | <u>Ala</u> | <u>Ser</u> | <u>Gln</u> | <u>Ser</u> | <u>Val</u> | <u>Asp</u> | <u>Tyr</u> | <u>Asp</u> | |
| 40 | | | | | 45 | | | | | 50 | | | |

| GGT | GAT | AGT | TAT | ATG | AAC | TGG | TAC | CAA | CAG | AAA | CCA | GGA | 195 |
|---|---|---|---|---|---|---|---|---|---|---|---|---|---|
| <u>Gly</u> | <u>Asp</u> | <u>Ser</u> | <u>Tyr</u> | <u>Met</u> | <u>Asn</u> | Trp | Tyr | Gln | Gln | Lys | Pro | Gly | |
| | | | 55 | | | | | 60 | | | | | 65 |

| CAG | CCA | CCC | AAA | CTC | CTC | ATC | TAT | GCT | GCA | TCC | AAT | CTA | 234 |
|---|---|---|---|---|---|---|---|---|---|---|---|---|---|
| Gln | Pro | Pro | Lys | Leu | Leu | Ile | Tyr | <u>Ala</u> | <u>Ala</u> | <u>Ser</u> | <u>Asn</u> | <u>Leu</u> | |
| | | | | 70 | | | | | 75 | | | | |

| GAA | TCT | GGG | ATC | CCA | GCC | AGG | TTT | AGT | GGC | AGT | GGG | TCT | 273 |
|---|---|---|---|---|---|---|---|---|---|---|---|---|---|
| <u>Glu</u> | <u>Ser</u> | Gly | Ile | Pro | Ala | Arg | Phe | Ser | Gly | Ser | Gly | Ser | |
| | | 80 | | | | | 85 | | | | | 90 | |

| GGG | ACA | GAC | TTC | ACC | CTC | AAC | ATC | CAT | CCT | GTG | GAG | GAG | 312 |
|---|---|---|---|---|---|---|---|---|---|---|---|---|---|
| Gly | Thr | Asp | Phe | Thr | Leu | Asn | Ile | His | Pro | Val | Glu | Glu | |
| | | | 95 | | | | | 100 | | | | | |

| GAG | GAT | GCT | GCA | ACC | TAT | TAC | TGT | CAG | CAA | AGT | AAT | GAG | 351 |
|---|---|---|---|---|---|---|---|---|---|---|---|---|---|
| Glu | Asp | Ala | Ala | Thr | Tyr | Tyr | Cys | <u>Gln</u> | <u>Gln</u> | <u>Ser</u> | <u>Asn</u> | <u>Glu</u> | |
| 105 | | | | | 110 | | | | | 115 | | | |

| GAT | CCT | CCG | ACG | TTC | GGT | GGA | GGC | ACC | AAG | CTG | GAA | ATC | 390 |
|---|---|---|---|---|---|---|---|---|---|---|---|---|---|
| <u>Asp</u> | <u>Pro</u> | <u>Pro</u> | <u>Thr</u> | Phe | Gly | Gly | Gly | Thr | Lys | Leu | Glu | Ile | |
| | | 120 | | | | | 125 | | | | | 130 | |

| AAA | CGG | | | | | | | | | | | | 396 |
|---|---|---|---|---|---|---|---|---|---|---|---|---|---|
| Lys | Arg | | | | | | | | | | | | |

Figure 2

Murine Antibody 3B9 Heavy Chain
Native Signal Sequence and Variable Region

Nucleotide Sequence SEQ ID NO: 3
Amino Acid Sequence SEQ ID NO: 4

| | |
|---|---|
| GAATTCGCGG CCGCTATGCA GGGACAATCA GCAGCAGCAA | 40 |

| | | | | | | | | | | | | |
|---|---|---|---|---|---|---|---|---|---|---|---|---|
| TGAGGAAGTA AGCCTGTGCA GAT | ATG | AAC | AGG | CTT | ACT | TCC | | | | | | 81 |
| | Met | Asn | Arg | Leu | Thr | Ser | | | | | | |
| | 1 | | | | 5 | | | | | | | |

| | | | | | | | | | | | |
|---|---|---|---|---|---|---|---|---|---|---|---|
| TCA | TTG | CTG | CTG | CTG | ATT | GTC | CCT | GCA | TAT | GTC | CTG | TCC | 120 |
| Ser | Leu | Leu | Leu | Leu | Ile | Val | Pro | Ala | Tyr | Val | Leu | Ser |
| | | | 10 | | | | 15 | | | | | |

| CAG | GTT | ACT | CTG | AAA | GAG | TCT | GGC | CCT | GGG | ATA | TTG | CAG | 159 |
|---|---|---|---|---|---|---|---|---|---|---|---|---|---|
| Gln | Val | Thr | Leu | Lys | Glu | Ser | Gly | Pro | Gly | Ile | Leu | Gln |
| 20 | | | | | 25 | | | | | 30 | | | |

| CCC | TCC | CAG | ACC | CTC | AGT | CTG | ACT | TGT | TCT | TTC | TCT | GGG | 198 |
|---|---|---|---|---|---|---|---|---|---|---|---|---|---|
| Pro | Ser | Gln | Thr | Leu | Ser | Leu | Thr | Cys | Ser | Phe | Ser | Gly |
| | | 35 | | | | 40 | | | | | 45 | | |

| TTT | TCA | CTG | AGC | ACT | TCT | GGT | ATG | GGT | GTG | AGC | TGG | ATT | 237 |
|---|---|---|---|---|---|---|---|---|---|---|---|---|---|
| Phe | Ser | Leu | Ser | Thr | Ser | Gly | Met | Gly | Val | Ser | Trp | Ile |
| | | | | 50 | | | | | 55 | | | | |

| CGT | CAG | CCT | TCA | GGA | AAG | GGT | CTG | GAG | TGG | CTG | GCA | CAC | 276 |
|---|---|---|---|---|---|---|---|---|---|---|---|---|---|
| Arg | Gln | Pro | Ser | Gly | Lys | Gly | Leu | Glu | Trp | Leu | Ala | His |
| | 60 | | | | | 65 | | | | | 70 | | |

| ATT | TAC | TGG | GAT | GAT | GAC | AAG | CGC | TAT | AAC | CCA | TCC | CTG | 315 |
|---|---|---|---|---|---|---|---|---|---|---|---|---|---|
| Ile | Tyr | Trp | Asp | Asp | Asp | Lys | Arg | Tyr | Asn | Pro | Ser | Leu |
| | | | 75 | | | | | 80 | | | | | |

| AAG | AGC | CGG | CTC | ACA | ATC | TCC | AAG | GAT | ACC | TCC | AGC | AAC | 354 |
|---|---|---|---|---|---|---|---|---|---|---|---|---|---|
| Lys | Ser | Arg | Leu | Thr | Ile | Ser | Lys | Asp | Thr | Ser | Ser | Asn |
| 85 | | | | | 90 | | | | | 95 | | | |

| CAG | GTA | TTC | CTC | AAG | ATC | ACC | AGT | GTG | GAC | ACT | GCA | GAT | 393 |
|---|---|---|---|---|---|---|---|---|---|---|---|---|---|
| Gln | Val | Phe | Leu | Lys | Ile | Thr | Ser | Val | Asp | Thr | Ala | Asp |
| | | | 100 | | | | 105 | | | | | 110 | |

| ACT | GCC | ACA | TAC | TAC | TGT | GCT | CGA | AGA | GAG | ACT | GTG | TTC | 432 |
|---|---|---|---|---|---|---|---|---|---|---|---|---|---|
| Thr | Ala | Thr | Tyr | Tyr | Cys | Ala | Arg | Arg | Glu | Thr | Val | Phe |
| | | | | 115 | | | | | 120 | | | | |

Figure 2 (con't)

```
TAC TGG TAC TTC GAT GTC TGG GGC GCA GGG ACC ACG GTC    471
Tyr Trp Tyr Phe Asp Val Trp Gly Ala Gly Thr Thr Val
    125             130             135

ACC GTC TCC TCA                                         483
Thr Val Ser Ser
            140
```

FIGURE 3

Human/Murine 3B9 Chimeric Antibody Heavy Chain
*Signal Sequence* and Variable Region Nucleotide Sequence SEQ ID NO: 9
Amino Acid Sequence SEQ ID NO:10

| | | | | | | | | | | | | |
|---|---|---|---|---|---|---|---|---|---|---|---|---|
| *ATG* | *GTG* | *TTG* | *CAG* | *ACC* | *CAG* | *GTC* | *TTC* | *ATT* | *TCT* | *CTG* | *TTG* | *CTC* | 39 |
| *Met* | *Val* | *Leu* | *Gln* | *Thr* | *Gln* | *Val* | *Phe* | *Ile* | *Ser* | *Leu* | *Leu* | *Leu* | |
| 1 | | | | 5 | | | | | 10 | | | |

| *TGG* | *ATC* | *TCT* | *GGT* | *GCC* | TAC | GGG | CAG | GTT | ACC | CTG | AAA | GAG | 78 |
| *Trp* | *Ile* | *Ser* | *Gly* | *Ala* | Tyr | Gly | Gln | Val | Thr | Leu | Lys | Glu | |
| | | 15 | | | | 20 | | | | 25 | | |

| TCT | GGC | CCT | GGG | ATA | TTG | CAG | CCC | TCC | CAG | ACC | CTC | AGT | 117 |
| Ser | Gly | Pro | Gly | Ile | Leu | Gln | Pro | Ser | Gln | Thr | Leu | Ser | |
| | | | 30 | | | | | 35 | | | | |

| CTG | ACT | TGT | TCT | TTC | TCT | GGG | TTT | TCA | CTG | AGC | ACT | TCT | 156 |
| Leu | Thr | Cys | Ser | Phe | Ser | Gly | Phe | Ser | Leu | Ser | <u>Thr</u> | <u>Ser</u> | |
| 40 | | | | | 45 | | | | | 50 | | |

| GGT | ATG | GGT | GTG | AGC | TGG | ATT | CGT | CAG | CCT | TCA | GGA | AAG | 195 |
| <u>Gly</u> | <u>Met</u> | <u>Gly</u> | <u>Val</u> | <u>Ser</u> | Trp | Ile | Arg | Gln | Pro | Ser | Gly | Lys | |
| | | | 55 | | | | | 60 | | | | 65 |

| GGT | CTG | GAG | TGG | CTG | GCA | CAC | ATT | TAC | TGG | GAT | GAT | GAC | 234 |
| Gly | Leu | Glu | Trp | Leu | Ala | <u>His</u> | <u>Ile</u> | <u>Tyr</u> | <u>Trp</u> | <u>Asp</u> | <u>Asp</u> | <u>Asp</u> | |
| | | | | 70 | | | | | 75 | | | |

| AAG | CGC | TAT | AAC | CCA | TCC | CTG | AAG | AGC | CGG | CTC | ACA | ATC | 273 |
| <u>Lys</u> | <u>Arg</u> | <u>Tyr</u> | <u>Asn</u> | <u>Pro</u> | <u>Ser</u> | <u>Leu</u> | <u>Lys</u> | <u>Ser</u> | Arg | Leu | Thr | Ile | |
| | | 80 | | | | | 85 | | | | 90 | |

| TCC | AAG | GAT | ACC | TCC | AGC | AAC | CAG | GTA | TTC | CTC | AAG | ATC | 312 |
| Ser | Lys | Asp | Thr | Ser | Ser | Asn | Gln | Val | Phe | Leu | Lys | Ile | |
| | | | | 95 | | | | | 100 | | | |

| ACC | AGT | GTG | GAC | ACT | GCA | GAT | ACT | GCC | ACA | TAC | TAC | TGT | 351 |
| Thr | Ser | Val | Asp | Thr | Ala | Asp | Thr | Ala | Thr | Tyr | Tyr | Cys | |
| 105 | | | | | 110 | | | | | 115 | | |

| GCT | CGA | AGA | GAG | ACT | GTG | TTC | TAC | TGG | TAC | TTC | GAT | GTC | 390 |
| Ala | Arg | <u>Arg</u> | <u>Glu</u> | <u>Thr</u> | <u>Val</u> | <u>Phe</u> | <u>Tyr</u> | <u>Trp</u> | <u>Tyr</u> | <u>Phe</u> | <u>Asp</u> | <u>Val</u> | |
| | | | 120 | | | | | 125 | | | | 130 |

| TGG | GGC | GCA | GGG | ACC | ACG | GTC | ACC | GTC | TCC | TCA | | | 423 |
| Trp | Gly | Ala | Gly | Thr | Thr | Val | Thr | Val | Ser | Ser | | | |
| | | | | 135 | | | | | 140 | | | |

FIGURE 4

Humanized 3B9 Antibody Heavy Chain
*Signal Sequence* and Variable Region

Nucleotide Sequence SEQ ID NO: 11
Amino Acid Sequence SEQ ID NO: 12

| | | | | | | | | | | | | |
|---|---|---|---|---|---|---|---|---|---|---|---|---|
| *ATG* | *GTG* | *TTG* | *CAG* | *ACC* | *CAG* | *GTC* | *TTC* | *ATT* | *TCT* | *CTG* | *TTG* | *CTC* | 39
| *Met* | *Val* | *Leu* | *Gln* | *Thr* | *Gln* | *Val* | *Phe* | *Ile* | *Ser* | *Leu* | *Leu* | *Leu* |
| 1 | | | | 5 | | | | | 10 | | | |

| | | | | | | | | | | | | |
|---|---|---|---|---|---|---|---|---|---|---|---|---|
| *TGG* | *ATC* | *TCT* | *GGT* | *GCC* | *TAC* | GGG | CAG | GTT | ACC | CTG | CGT | GAA | 78
| *Trp* | *Ile* | *Ser* | *Gly* | *Ala* | *Tyr* | Gly | Gln | Val | Thr | Leu | Arg | Glu |
| | | 15 | | | | 20 | | | | 25 | | |

| | | | | | | | | | | | |
|---|---|---|---|---|---|---|---|---|---|---|---|
| TCC | GGT | CCG | GCA | CTA | GTT | AAA | CCG | ACC | CAG | ACC | CTG | ACG | 117
| Ser | Gly | Pro | Ala | Leu | Val | Lys | Pro | Thr | Gln | Thr | Leu | Thr |
| | | | 30 | | | | | 35 | | | | |

| | | | | | | | | | | | |
|---|---|---|---|---|---|---|---|---|---|---|---|
| TTA | ACC | TGC | ACC | TTC | TCC | GGT | TTC | TCC | CTG | TCG | ACC | TCC | 156
| Leu | Thr | Cys | Thr | Phe | Ser | Gly | Phe | Ser | Leu | Ser | <u>Thr</u> | <u>Ser</u> |
| 40 | | | | | 45 | | | | | 50 | | |

| | | | | | | | | | | | |
|---|---|---|---|---|---|---|---|---|---|---|---|
| GGT | ATG | GGT | GTT | TCC | TGG | ATC | CGT | CAG | CCG | CCG | GGT | AAA | 195
| <u>Gly</u> | <u>Met</u> | <u>Gly</u> | <u>Val</u> | <u>Ser</u> | Trp | Ile | Arg | Gln | Pro | Pro | Gly | Lys |
| | | 55 | | | | | 60 | | | | | 65 |

| | | | | | | | | | | | |
|---|---|---|---|---|---|---|---|---|---|---|---|
| GGT | CTA | GAA | TGG | CTG | GCT | CAC | ATC | TAC | TGG | GAC | GAC | GAC | 234
| Gly | Leu | Glu | Trp | Leu | Ala | <u>His</u> | <u>Ile</u> | <u>Tyr</u> | <u>Trp</u> | <u>Asp</u> | <u>Asp</u> | <u>Asp</u> |
| | | | | 70 | | | | | 75 | | | |

| | | | | | | | | | | | |
|---|---|---|---|---|---|---|---|---|---|---|---|
| AAA | CGT | TAC | AAC | CCG | AGC | CTG | AAA | TCC | CGT | CTG | ACG | ATA | 273
| <u>Lys</u> | <u>Arg</u> | <u>Tyr</u> | <u>Asn</u> | <u>Pro</u> | <u>Ser</u> | <u>Leu</u> | <u>Lys</u> | <u>Ser</u> | Arg | Leu | Thr | Ile |
| | | 80 | | | | | 85 | | | | | 90 |

| | | | | | | | | | | | |
|---|---|---|---|---|---|---|---|---|---|---|---|
| TCC | AAA | GAC | ACC | TCC | CGT | AAC | CAG | GTT | GTT | CTG | ACC | ATG | 312
| Ser | Lys | Asp | Thr | Ser | Arg | Asn | Gln | Val | Val | Leu | Thr | Met |
| | | | 95 | | | | | 100 | | | | |

| | | | | | | | | | | | |
|---|---|---|---|---|---|---|---|---|---|---|---|
| ACT | AAC | ATG | GAC | CCG | GTT | GAC | ACC | GCT | ACC | TAC | TAC | TGC | 351
| Thr | Asn | Met | Asp | Pro | Val | Asp | Thr | Ala | Thr | Tyr | Tyr | Cys |
| 105 | | | | | 110 | | | | | 115 | | |

| | | | | | | | | | | | |
|---|---|---|---|---|---|---|---|---|---|---|---|
| GCT | CGA | CGC | GAA | ACC | GTT | TTC | TAC | TGG | TAC | TTC | GAC | GTT | 390
| Ala | Arg | <u>Arg</u> | <u>Glu</u> | <u>Thr</u> | <u>Val</u> | <u>Phe</u> | <u>Tyr</u> | <u>Trp</u> | <u>Tyr</u> | <u>Phe</u> | <u>Asp</u> | <u>Val</u> |
| | | | 120 | | | | | 125 | | | | 130 |

| | | | | | | | | | | |
|---|---|---|---|---|---|---|---|---|---|---|
| TGG | GGT | CGT | GGT | ACC | CCA | GTT | ACC | GTG | AGC | TCA | 423
| Trp | Gly | Arg | Gly | Thr | Pro | Val | Thr | Val | Ser | Ser |
| | | | | 135 | | | | | 140 | |

FIGURE 5

Humanized 3B9 Antibody Light Chain
*Signal Sequence* and Variable Region

Nucleotide Sequence SEQ ID NO: 13
Amino Acid Sequence SEQ ID NO: 14

| | | | | | | | | | | | |
|---|---|---|---|---|---|---|---|---|---|---|---|
| *ATG* | *GGA* | *TGG* | *AGC* | *TGT* | *ATC* | *ATC* | *CTC* | *TTC* | *TTG* | *GTA* | *GCA* | *ACA* | 39 |
| *Met* | *Gly* | *Trp* | *Ser* | *Cys* | *Ile* | *Ile* | *Leu* | *Phe* | *Leu* | *Val* | *Ala* | *Thr* |
| 1 | | | | 5 | | | | | 10 | | | |

| *GCT* | *ACA* | *GGT* | *GTC* | *CAC* | *TCC* | GAT | ATC | GTG | ATG | ACC | CAG | TCT | 78 |
| *Ala* | *Thr* | *Gly* | *Val* | *His* | *Ser* | Asp | Ile | Val | Met | Thr | Gln | Ser |
| | 15 | | | | 20 | | | | 25 | | | |

| CCA | GAC | TCG | CTA | GCT | GTG | TCT | CTG | GGC | GAG | AGG | GCC | ACC | 117 |
| Pro | Asp | Ser | Leu | Ala | Val | Ser | Leu | Gly | Glu | Arg | Ala | Thr |
| | | | 30 | | | | 35 | | | | | |

| ATC | AAC | TGC | AAG | GCC | TCC | CAA | AGT | GTT | GAT | TAT | GAT | GGT | 156 |
| Ile | Asn | Cys | <u>Lys</u> | <u>Ala</u> | <u>Ser</u> | <u>Gln</u> | <u>Ser</u> | <u>Val</u> | <u>Asp</u> | <u>Tyr</u> | <u>Asp</u> | <u>Gly</u> |
| 40 | | | | | 45 | | | | | 50 | | |

| GAT | AGT | TAT | ATG | AAC | TGG | TAT | CAG | CAG | AAA | CCC | GGG | CAG | 195 |
| <u>Asp</u> | <u>Ser</u> | <u>Tyr</u> | <u>Met</u> | <u>Asn</u> | Trp | Tyr | Gln | Gln | Lys | Pro | Gly | Gln |
| | | 55 | | | | | 60 | | | | | 65 |

| CCT | CCT | AAG | TTG | CTC | ATT | TAC | GCT | GCA | TCC | AAT | CTA | GAA | 234 |
| Pro | Pro | Lys | Leu | Leu | Ile | Tyr | <u>Ala</u> | <u>Ala</u> | <u>Ser</u> | <u>Asn</u> | <u>Leu</u> | <u>Glu</u> |
| | | | | 70 | | | | | 75 | | | |

| TCT | GGG | GTA | CCT | GAC | CGA | TTC | AGT | GGC | AGC | GGG | TCT | GGG | 273 |
| <u>Ser</u> | Gly | Val | Pro | Asp | Arg | Phe | Ser | Gly | Ser | Gly | Ser | Gly |
| | 80 | | | | | 85 | | | | | 90 | |

| ACA | GAT | TTC | ACT | CTC | ACC | ATC | AGC | AGC | CTG | CAG | GCT | GAA | 312 |
| Thr | Asp | Phe | Thr | Leu | Thr | Ile | Ser | Ser | Leu | Gln | Ala | Glu |
| | | | 95 | | | | | 100 | | | | |

| GAT | GTG | GCA | GTA | TAC | TAC | TGT | CAG | CAA | AGT | AAT | GAG | GAT | 351 |
| Asp | Val | Ala | Val | Tyr | Tyr | Cys | <u>Gln</u> | <u>Gln</u> | <u>Ser</u> | <u>Asn</u> | <u>Glu</u> | <u>Asp</u> |
| 105 | | | | | 110 | | | | | 115 | | |

| CCT | CCG | AGG | TTC | GGC | GGA | GGG | ACC | AAG | GTG | GAG | ATC | AAA | 390 |
| <u>Pro</u> | <u>Pro</u> | <u>Arg</u> | Phe | Gly | Gly | Gly | Thr | Lys | Val | Glu | Ile | Lys |
| | | 120 | | | | | 125 | | | | | 130 |

| CGT | | | | | | | | | | | | | 393 |
| Arg | | | | | | | | | | | | |

FIGURE 6A

Signal Sequence
Nucleotide SEQ ID NO:5
Amino Acid SEQ ID NO:6

```
ATG GTG TTG CAG ACC CAG GTC TTC ATT TCT CTG TTG CTC    39
Met Val Leu Gln Thr Gln Val Phe Ile Ser Leu Leu Leu
 1               5                   10

TGG ATC TCT GGT GCC TAC
Trp Ile Ser Gly Ala Tyr
        15
```

FIGURE 6B

Signal Sequence
Nucleotide SEQ ID NO:7
Amino Acid SEQ ID NO:8

```
ATG GGA TGG AGC TGT ATC ATC CTC TTC TTG GTA GCA ACA    39
Met Gly Trp Ser Cys Ile Ile Leu Phe Leu Val Ala Thr
 1               5                   10

GCT ACA GGT GTC CAC TCC GAT ATC GTG ATG ACC CAG TCT    78
Ala Thr Gly Val His Ser Asp Ile Val Met Thr Gln Ser
        15              20
```

RECOMBINANT IL4 ANTIBODIES USEFUL IN TREATMENT OF IL4 MEDIATED DISORDERS

CROSS REFERENCE TO RELATED APPLICATIONS

This application is a continuation of application Ser. No. 10/723,872, filed Nov. 26, 2003, now abandoned; which is a continuation of prior application Ser. No. 09/879,461, filed Jun. 12, 2001, now abandoned; which is a continuation of application Ser. No. 09/426,814, filed Oct. 22, 1999, now abandoned; which is a continuation of application Ser. No. 08/612,929, filed 30 Apr. 1996, now abandoned; which is a 371 of PCT/US94/10308, filed 7 Sep. 1994; which is a continuation-in-part of application Ser. No. 08/136,783, filed Oct. 14, 1993, now abandoned; which is a continuation of application Ser. No. 08/117,366 filed Sep. 7, 1993, now abandoned; all of which are hereby incorporated by reference in their entirety.

FIELD OF THE INVENTION

The present invention relates generally to the field of fusion proteins, and to proteins useful in treatment and diagnosis of conditions mediated by IL4 and excess IgE production, and more specifically to chimeric and humanized IL4 antibodies.

BACKGROUND OF THE INVENTION

Atopic allergic diseases range from the relatively minor, such as seasonal rhinitis and conjunctivitis, to the more serious, such as atopic dermatitis and atopic asthma, and life threatening, such as anaphylactic shock. Linking these conditions is the immune response of the body to allergens, which response involves the production of immunoglobulin E (IgE) antibodies in genetically predisposed individuals (atopy). Inhibition of IgE production has long been a goal in specific immunotherapy of allergic disease using desensitization vaccines. However, in recent years the safety and efficacy of vaccine therapy have been questioned, but the desire to reduce IgE levels has not waned.

Interleukin 4 (IL4) is a protein mediator in the lymphoid system. Studies of lymphocytes from atopic individuals have revealed the presence of higher than normal numbers of T lymphocytes with the ability to secrete IL4 in response to stimulation, and larger quantities of IL4 secreted following stimulation.

Anti-IL4 antibody has been found to inhibit IgE, but not $IgG_1$ or $IgG_2$, [Finkelman et al, *Ann. Rev. Immunol.*, 8:303 (1990)], and the production of IL5 secreting T cells [Maggi et al, *J. Immunol.*, 148:2142 (1992)]. Further, recent data suggests that IL4 may affect eosinophil accumulation in tissues. See, e.g. Tepper et al, *Cell*, 62:457 (1990); Tepper et al, *Cell*, 57:503 (1989).

There remains a need in the art for a high affinity IL4 antagonist, which would reduce eosinophil inflammation both by reducing the proliferation of IL5 secreting cells, and by inhibiting an adherence mechanism whereby eosinophils may be accumulating in tissues, and can be used to treat, prevent or diagnose allergic reactions.

SUMMARY OF THE INVENTION

In a first aspect, the present invention provides a fusion protein having a binding affinity for human interleukin-4 which comprises complementarity determining regions (CDRs) derived from a non-human neutralizing monoclonal antibody (MAb) characterized by a dissociation constant equal to or less than $2 \times 10^{-10}$ M for human IL4, and a first fusion partner in which at least one, and preferably all complementarity determining regions (CDRs) of the first fusion partner are replaced by CDRs from the non-human monoclonal antibody (MAb). The non-human neutralizing monoclonal antibody may be selected from the group consisting of 3B9 and 6A1 as described more fully in the Detailed Description. Preferably, the fusion protein is operatively linked to a second fusion protein as well, which comprises all or a part of an immunoglobulin constant chain.

In a related aspect, the present invention provides CDRs derived from non-human neutralizing monoclonal antibodies (MAb) characterized by a dissociation constant equal to or less than $2 \times 10^{-10}$ M for human IL4, and nucleic acid molecules encoding such CDRs.

In another aspect, the invention provides humanized antibodies having at least one, and preferably six, complementarity determining regions (CDRs) derived from non-human neutralizing monoclonal antibodies (MAb) characterized by a dissociation constant equal to or less than $2 \times 10^{-10}$ M for human IL4.

In still another aspect, there is provided a chimeric antibody containing human heavy and light chain constant regions and heavy and light chain variable regions derived from non-human neutralizing monoclonal antibodies (MAb) characterized by a dissociation constant equal to or less than $2 \times 10^{-10}$ M for human IL4.

In still another aspect, the present invention provides a pharmaceutical composition which contains one (or more) of the above-described fusion proteins or MAbs (e.g., humanized, chimeric, etc.) and a pharmaceutically acceptable carrier.

In a further aspect, the present invention provides a method for treating and/or preventing allergic conditions in humans by administering to said human an effective amount of pharmaceutical composition of the invention.

In yet another aspect, the present invention provides methods for, and components useful in, the recombinant production of the fusion proteins, MAbs (e.g., humanized, chimeric, etc.), CDRs thereof, a Fab, or F(ab)$_2$, or analog thereof which is derived from non-human neutralizing monoclonal antibodies (MAb) characterized by a dissociation constant equal to or less than $2 \times 10^{-10}$ M for human IL4. These components include isolated nucleic acid sequences encoding same, recombinant plasmids containing the nucleic acid sequences under the control of selected regulatory sequences capable of directing the expression thereof in host cells, and host cells (preferably mammalian) transfected with the recombinant plasmids. The production method involves culturing a transfected host cell line of the present invention under conditions such that an antibody, preferably a humanized antibody, is expressed in said cells and isolating the expressed product therefrom.

In yet another aspect of the invention is a method to diagnose allergies and other conditions associated with excess immunoglobulin E production in a human which comprises contacting a sample of biological fluid with the fusion proteins, MAbs (e.g., humanized, chimeric, etc.) and Fabs of the instant invention and assaying for the occurrence of binding between said fusion protein, MAb or Fab and human interleukin 4.

In another related aspect is provided a method for screening monoclonal antibodies which have a high titer for human interleukin 4 which comprises: (a) preparing a hybridoma cell line characterized by secretion of a monoclonal antibody to human interleukin 4; and (b) screening said hybridoma cell line with aldehyde-coupled human interleukin-4 or biotinylated human interleukin-4. Preferably, the hybridoma cell line is screened with biotinylated human interleukin-4.

Also provided is a neutralizing MAb having high affinity for IL4, a Fab fragment or a F(ab')$_2$ fragment thereof, produced by screening a library of hydridoma products with aldehyde-coupled human interleukin-4 or biotinylated human IL4.

In another aspect, the present invention provides rodent neutralizing monoclonal antibodies specific for human interleukin-4 and having a binding affinity characterized by a dissociation constant equal to or less than about $2 \times 10^{-10}$ M. Exemplary of such monoclonal antibodies is the murine MAb, 3B9, and the rat MAb, 6A1 and other MAbs have the same identifying characteristics (i.e., binds to the same epitope(s) as 3B9 or 6A1 with a specificity for human IL4 and a dissociation constant equal to or less than about $2 \times 10^{-10}$ M). Another aspect of the invention is hybridoma 3426A11C1B9.

Other aspects and advantages of the present invention are described further in the following detailed description of the preferred embodiments thereof.

BRIEF DESCRIPTION OF THE DRAWINGS

FIG. 1 [SEQ ID NOS: 1 and 2] illustrates the light chain variable region (amino acids 21-132) for the murine IL4 antibody 3B9, and the human/murine 3B9 chimeric antibody as well as the native signal sequence (amino acids 1-20). The underlined portions indicate the CDRs [SEQ ID NOS: 15 and 16; SEQ ID NOS: 17 and 18; and SEQ ID NOS: 19 and 20].

FIG. 2 [SEQ ID NOS: 3 and 4] illustrates the heavy chain variable region (amino acids 20-140) of the murine 3B9, and the native signal sequence (amino acids 1-19). The underlined portions indicate the CDRs [SEQ ID NOS: 21 and 22; SEQ ID NOS: 23 and 24; and SEQ ID NOS: 25 and 26].

FIG. 3 [SEQ ID NOS: 9 and 10] illustrates the heavy chain variable region (amino acids 21-141) of the human/murine 3B9 chimeric antibody and its signal sequence (amino acids 1-19: SEQ ID NOS: 5 and 6). The underlined portions indicate the CDRs derived from 3B9 [SEQ ID NOS: 21 and 22; SEQ ID NOS: 23 and 24; and SEQ ID NOS: 25 and 26].

FIG. 4 [SEQ ID NOS: 11 and 12] illustrates the heavy chain variable region (amino acids 20-141) of the humanized 3B9 antibody and a signal sequence (amino acids 1-19: SEQ ID NOS: 5 and 6). The underlined portions indicate the CDRs derived from 3B9 [SEQ ID NOS: 54 and 22; SEQ ID NOS: 55 and 24; and SEQ ID NOS: 56 and 26].

FIG. 5 [SEQ ID NOS: 13 and 14] illustrates the light chain variable region (amino acids 21-131) of the humanized 3B9 antibody and a signal sequence (amino acids 1-20; SEQ ID NOS: 7 and 8). The underlined portions indicate the CDRs derived from 3B9 [SEQ ID NOS: 53 and 16; SEQ ID NOS: 17 and 18; and SEQ ID NOS: 27 and 28].

FIG. 6A [SEQ ID NOS: 5 and 6] is a heavy chain signal sequence used in Example 4 below.

FIG. 6B [SEQ ID NOS: 7 and 8] is a light chain signal sequence used in Example 4 below.

DETAILED DESCRIPTION OF THE INVENTION

Figure 7:
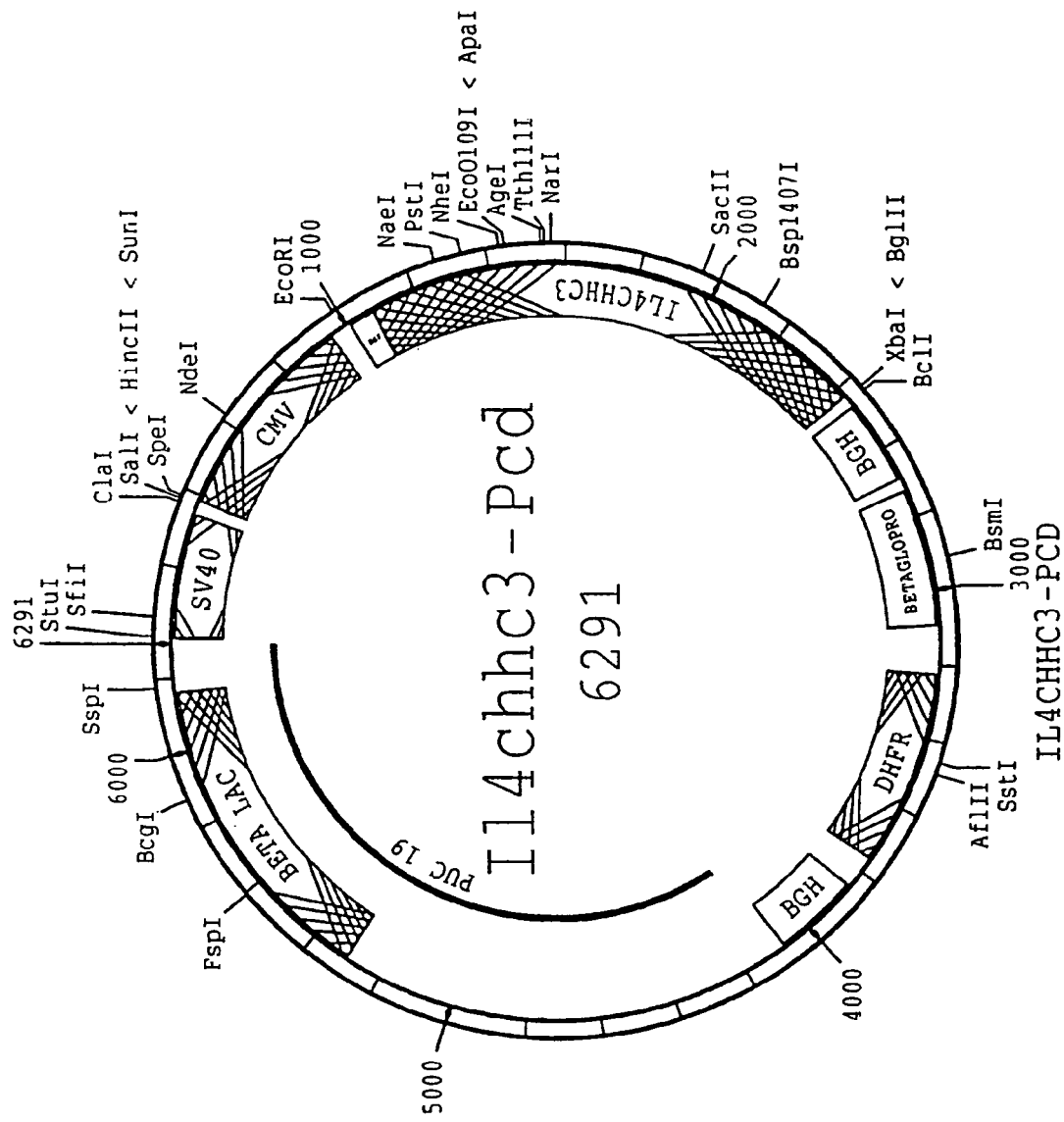
FIG. 7 is a schematic drawing of plasmid pIL4chhc3-pcd employed to express a chimeric IL4 heavy chain in mammalian cells. The plasmid contains a beta lactamase gene (BETA LAC), an SV-40 origin of replication (SV40), a cytomegalovirus promoter sequence (CMV), a signal sequence, the chimeric variable heavy chain of SEQ ID NOS: 9 and 10, a human heavy chain constant region, a poly A signal from bovine growth hormone (BGH), a betaglobin promoter (beta glopro), a dihydrofolate reductase gene (DHFR), and another BGH sequence poly A signal in a pUC19 background.

The present invention provides a variety of antibodies, fragments thereof, and fusion proteins particularly humanized antibodies, which are characterized by human IL4 binding specificity, neutralizing activity, and high affinity for human IL4 as exemplified in murine MAb 3B9 or the rat MAb 6A1. These products are useful in therapeutic and pharmaceutical compositions for treating IL4-mediated and IgE-mediated allergic reactions. These products are also useful in the diagnosis of an IL4 mediated condition by measurement (e.g., by enzyme linked immunosobent assay (ELISA)) of circulating, endogenous IL4 levels in humans.

I. Definitions.

"Fusion protein" refers to a protein encoded by a fusion molecule, which may be obtained by expression in a selected host cell. Such fusion proteins are engineered antibodies, e.g., chimeric or humanized antibodies, or antibody fragments lacking all or part of an immunoglobulin constant region, e.g., Fv, Fab, or F(ab)$_2$ and the like.

"Fusion molecule" refers to a nucleic acid sequence encoding the complementarity determining regions (CDRs) from a non-human immunoglobulin that are inserted into a first fusion partner comprising human variable framework sequences. Optionally, the first fusion partner is operatively linked to a second fusion partner.

"First fusion partner" refers to a nucleic acid sequence encoding a human framework or human immunoglobulin variable region in which the native (or naturally-occurring) CDRs are replaced by the CDRs of a donor antibody. The human variable region can be an immunoglobulin heavy chain, a light chain (or both chains), an analog or functional fragments thereof. Such CDRs or CDR regions, located within the variable region of antibodies (immunoglobulins) can be determined by known methods in the art. For example Kabat et al., [*Sequences of Proteins of Immunological Interest,* 4th Ed., U.S. Department of Health and Human Services, National Institues of Health (1987)], disclose rules for locating CDRs. In addition, computer programs are known which are useful for identifying CDR regions/structures.

The term "high titer" refers to an antibody having a binding affinity characterized by a $K_d$ equal to or less than $2 \times 10^{-10}$ M for human IL4.

By "binding specificity for human IL4" is meant a high titer (or affinity) for human, not bovine or murine, IL4.

"Second fusion partner" refers to another nucleotide sequence encoding a protein or peptide to which the first fusion partner is fused in frame or by means of an optional conventional linker sequence (i.e., operatively linked). Preferably it is an immunoglogulin. The second fusion partner may include a nucleic acid sequence encoding the entire constant region for the same (i.e., homologous—the first and second fusion proteins are derived from the same source) or an additional (i.e., heterologous) antibody of interest. It may be an immunoglobulin heavy chain or light chain (or both chains as part of a single polypeptide). The second fusion partner is not limited to a particular immunoglobulin class or isotype. In addition, the second fusion partner may comprise part of an immunoglobulin constant region, such as found in a Fab, or F(ab)$_2$ (i.e., a discrete part of an appropriate human constant region or framework region). Such second fusion partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fab, or F(ab)$_2$ are used with their standard meanings (see, e.g., Harlow et al., *Antibodies A Laboratory Manual*, Cold Spring Harbor Laboratory, (1988)).

As used herein, an "engineered antibody" describes a type of fusion protein, i.e., a synthetic antibody (e.g., a chimeric or humanized antibody) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin. In addition, framework support residues may be altered to preserve binding affinity (see, e.g., Queen et al., *Proc. Natl Acad Sci USA*, 86:10029-10032 (1989), Hodgson et al., *Bio/Technology* 2:421 (1991)).

The term "donor antibody" refers to an antibody (polyclonal, monoclonal, or recombinant) which contributes the nucleic acid sequences of its variable regions, CDRs, or other functional fragments or analogs thereof to a first fusion partner, so as to provide the fusion molecule and resulting expressed fusion protein with the antigenic specificity and neutralizing activity characteristic of the donor antibody. One donor antibody suitable for use in this invention is a non-human neutralizing monoclonal antibody (i.e., murine) designated as 3B9. The antibody 3B9 is defined as a high titer, human-IL4 specific (i.e., does not recognize bovine or murine IL4), neutralizing antibody of isotype IgG$_1$ having the variable light chain DNA and amino acid sequences of SEQ ID NOS: 1 and 2, and the variable heavy chain DNA and amino acid sequences of SEQ ID NOS: 3 and 4 on a suitable murine IgG constant region.

The term "acceptor antibody" refers to an antibody (polyclonal, monoclonal, or recombinant) heterologous to the donor antibody, which contributes all (or any portion, but preferably all) of the nucleic acid sequences encoding its heavy and/or light chain framework regions and/or its heavy and/or light chain constant regions to the second fusion partner. Preferably a human antibody is the acceptor antibody.

"CDRs" are defined as the complementarity determining region amino acid sequences of an antibody which are the hypervariable regions of immunoglobulin heavy and light chains. See, e.g., Kabat et al., *Sequences of Proteins of Immunological Interest*, 4th Ed., U.S. Department of Health and Human Services, National Institues of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate).

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

By 'sharing the antigen binding specificity or neutralizing ability' is meant, for example, that although MAb 3B9 may be characterized by a certain level of antigen affinity, and a CDR encoded by a nucleic acid sequence of 3B9 in an appropriate structural environment may have a lower or higher affinity, it is expected that CDRs of 3B9 in such environments will nevertheless recognize the same epitope(s) as 3B9. Exemplary heavy chain CDRs of 3B9 include SEQ ID NO: 22; SEQ ID NO: 24; SEQ ID, NO: 26; and exemplary light chain CDRs of 3B9 include SEQ ID NO: 16; SEQ ID NO: 18; and SEQ ID NO: 20.

A "functional fragment" is a partial heavy or light chain variable sequence (e.g., minor deletions at the amino or carboxy terminus of the immunogloblin variable region) which retains the same antigen binding specificity and/or neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high titer or affinity, of the unmodified sequence. For example, silent mutations can be constructed, via substitutions, to create endonuclease restriction sites within or surrounding CDR regions.

Analogs may also arise as allelic variations. An "allelic variation or modification" is an alteration in the nucleic acid sequence encoding the amino acid or peptide sequences of the invention. Such variations or modifications may be due to degeneracies in the genetic code or may be deliberately engineered to provide desired characteristics. These variations or modifications may or may not result in alterations in any encoded amino acid sequence. For example, the amino acid sequences of the light chain CDR SEQ ID NO: 16 are identical for the native murine and humanized 3B9 antibody. However, this CDR sequence is encoded by both SEQ ID NO: 15 and SEQ ID NO: 53. Similarly, CDR SEQ ID NO: 22 is encoded both by SEQ ID NO: 21 and SEQ ID NO: 54; CDR SEQ ID NO: 24 is encoded both by SEQ ID NO: 23 and SEQ ID NO: 55; and CDR SEQ ID NO: 26 is encoded both by SEQ ID NO: 25 and SEQ ID NO: 56.

The term "effector agents" refers to non-protein carrier molecules to which the fusion proteins, and/or natural or synthetic light or heavy chain of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore [Pharmacia] system, or other non-protein substances useful in the medical field and safe for administration to humans and animals. Other effector agents may include a macrocycle, for chelating a heavy metal atom, or radioisotopes. Such effector agents may also be useful to increase the half-life of the fusion proteins, e.g., polyethylene glycol.

II. High Affinity IL4 Monoclonal Antibodies

For use in constructing the antibodies, fragments and fusion proteins of this invention, a non-human species (for example, bovine, ovine, primate, rodent (e.g., murine and rat), etc.) may be employed to generate a desirable immunoglobulin upon presentment with native human IL4 or a peptide epitope therefrom. Conventional hybridoma techniques are employed to provide a hybridoma cell line secreting a non-human MAb to IL4. Such hybridomas are then screened using IL4 covalently attached to 96-well plates or alternatively with biotinylated IL4 for use in a screening assay, as described in detail in Example 2 below. Thus one feature of the instant invention is a method to detect MAbs for human IL4 in which the assay systems avoid denaturing of IL4. In such a manner, it was discovered that high titer (or high affinity) MAbs to human IL4 can be detected.

As one example, the production of a high titer, neutralizing MAb from a murine donor is disclosed for the first time. MAb 3B9, which is a desirable murine (donor) antibody for use in developing a chimeric or humanized antibody, is described in detail in Example 1 below. The 3B9 MAb is characterized by an antigen binding specificity for human IL4, with a $K_d$ of less than $2.0 \times 10^{-10}$ M (about $1.8 \times 10^{-10}$ M) for IL4. The $K_d$ for IL4 of a Fab fragment of this 3B9 is less than about $3 \times 10^{-10}$ M. The epitope of this antibody could not be mapped to IL4 with linear peptides, and hence the epitope is considered to bind to a non-contiguous epitope. The pattern of binding suggests a binding site at the B-C loop (residues 60-69)→C helix (residues 70-93) region. These regions refer to the map designations provided in Cook et al, *J. Mol. Biol.*, 218:675-678 (1991), Walter et al, *J. Biol. Chem.*, 267:20371-20376 (1992), Wlodaver et al, *FEBS Lett.*, 309:59-64 (1992), Redfield et al, *Biochem.*, 30:11029-11035 (1991), Smith et al, *J. Mol. Biol.*, 224:899-904 (1992), Garrett et al, (1992), and Powers et al, *Biochem.*, 31:4334-4346 (1992) and *Science*, 256:1673-1677 (1992), incorporated by reference herein.

Another desirable donor antibody is the rat MAb, 6A1. The production of this MAb is provided below in Example 7. This MAb is characterized by being isotype $IgG_{2a}$, and having a dissociation constant for hIL4 of less than 2.0×10–10 M (about $1.6 \times 10^{-10}$ M). As with 3B9, the target epitope of this 6A1 does not map with IL4 linear peptides, and the epitope is therefore considered to be non-contiguous and three dimensional. The pattern of binding to IL4 muteins and its biological activity indicates binding in the D helix region of human IL4 (amino acid residues 109-127), most likely around the tyrosine at amino acid residue #124.

This invention is not limited to the use of the 3B9 MAb, the 6A1 MAb, or its hypervariable (i.e., CDR) sequences. Any other appropriate high titer IL4 antibodies characterized by a dissociation constant equal or less than $2.0 \times 10^{-10}$ M for human IL4 and corresponding anti-IL4 CDRs may be substituted therefor. Wherever in the following description the donor antibody is identified as 3B9 or 6A1, this designation is made for illustration and simplicity of description only.

III. Antibody Fragments

The present invention also includes the use of Fab fragments or F(ab')$_2$ fragments derived from MAbs directed against human IL4. These fragments are useful as agents protective in vivo against IL4- and IgE-mediated conditions or in vitro as part of an IL4 diagnostic. A Fab fragment contains the entire light chain and amino terminal portion of the heavy chain; and an F(ab')$_2$ fragment is the fragment formed by two Fab fragments bound by disulfide bonds. MAbs 3B9, 6A1, and other similar high affinity, IL4 binding antibodies, provide sources of Fab fragments and F(ab')$_2$ fragments which can be obtained by conventional means, e.g., cleavage of the MAb with the appropriate proteolytic enzymes, papain and/or pepsin, or by recombinant methods. These Fab and F(ab')$_2$ fragments are useful themselves as therapeutic, prophylactic or diagnostic agents, and as donors of sequences including the variable regions and CDR sequences useful in the formation of recombinant or humanized antibodies as described herein.

IV. Anti-IL4 Amino Acid and Nucleotide Sequences of Interest

The MAb 3B9 or other antibodies described above may contribute sequences, such as variable heavy and/or light chain peptide sequences, framework sequences, CDR sequences, functional fragments, and analogs thereof, and the nucleic acid sequences encoding them, useful in designing and obtaining various fusion proteins (including engineered antibodies) which are characterized by the antigen binding specificity of the donor antibody.

As one example, the present invention thus provides variable light chain and variable heavy chain sequences from the IL4 murine antibody 3B9 and sequences derived therefrom. The heavy chain variable region of 3B9 is characterized by amino acid residues 20 to 140 of SEQ ID NO: 4. The CDR regions are indicated by underlining in FIG. 2 and are provided in SEQ ID NO: 22; SEQ ID NO: 24; and SEQ ID NO: 26. The light chain clone variable region of 3B9 is characterized by amino acid residues 21 to 132 of FIG. 1 [SEQ ID NO: 2]. The CDR regions are from amino acid residues 44-58 [SEQ ID NO: 16]; 74-80 [SEQ ID NO: 18]; and 113-121 [SEQ ID NO: 20].

Chimeric heavy chain variable region and signal nucleotide and amino acid sequences are provided. These sequences are identical to the 3B9 heavy chain with the exception of the signal sequence. The chimeric heavy chain signal sequence is provided in SEQ ID NOS: 5 and 6. The CDR regions are indicated by underlining in FIG. 3 and are identical in amino acid sequence to the native murine CDRs [SEQ ID NOS: 21-26]. The chimeric light chain variable region nucleotide and amino acid sequences are identical to the unmodified 3B9 sequences (amino acid residues 21-132 of SEQ ID NO: 2), making use of the natural mouse signal sequences (amino acid residues 1-20 of SEQ ID NO: 2).

A humanized heavy chain variable region and signal sequences are illustrated in FIG. 4 [SEQ ID NO: 11 and 12]. The signal sequence is also provided in SEQ ID NO: 5 and 6. Other suitable signal sequences, known to those of skill in the art, may be substituted for the signal sequences exemplified herein. The CDR amino acid sequences of this construct are identical to the native murine and chimeric heavy chain CDRs and are provided by SEQ ID NO: 22 (encoded by SEQ ID NO:

54), SEQ ID NO: 24 (encoded by SEQ ID NO: 55), and SEQ ID NO: 56 (encodes SEQ ID NO: 26).

An exemplary (synthetic) humanized light chain variable sequence is illustrated in FIG. 5 [SEQ ID NOS: 13 and 14]. The signal sequence spans amino acid residues 1 to 19 of SEQ ID NO: 8. The CDR sequences of this figure are designated by underlining and differ from the CDR of the native murine CDR by a single amino acid of SEQ ID NO: 20. Thus, the CDRs of the humanized light chain are provided by SEQ ID NO: 53 and 16, SEQ ID NO: 17 and 18, and SEQ ID NO: 27 and 28. This difference is described in detail in Example 3.

The nucleic acid sequences of this invention, or fragments thereof, encoding the variable light chain and heavy chain peptide sequences are used in unmodified form or are synthesized to introduce desirable modifications, e.g., restriction sites. The isolated naturally-occurring or alternatively synthetic nucleic acid sequences, which are derived from MAb 3B9 or from other desired high titer IL4 antibodies may optionally contain restriction sites to facilitate insertion or ligation into a suitable nucleic acid sequence such as encoding a desired antibody framework region, ligation with mutagenized CDRs or fusion with a nucleic acid sequence encoding a selected second fusion partner.

Taking into account the degeneracy of the genetic code, various coding sequences may be constructed which encode the variable heavy and light chain amino acid sequences, and CDR sequences of the invention as well as functional fragments and analogs thereof which share the antigen specificity of the donor antibody. The isolated nucleic acid sequences of this invention, or fragments thereof, encoding the variable chain peptide sequences or CDRs can be used to produce fusion proteins, chimeric or humanized antibodies, or other engineered antibodies of this invention when operatively combined with a second fusion partner.

These sequences are also useful for mutagenic introduction of specific changes within the nucleic acid sequences encoding the CDRs or framework regions, and for incorporation of the resulting modified or fusion nucleic acid sequence into a plasmid for expression. For example, silent substitutions in the nucleotide sequence of the framework and CDR-encoding regions were used to create restriction enzyme sites which facilitated insertion of mutagenized CDR (and/or framework) regions. These CDR regions were used in the construction of a humanized antibody of this invention.

It should be noted that in addition to isolated nucleic acid sequences encoding portions of the fusion protein and antibodies described herein, other such nucleic acid sequences may be employed, such as those complementary to the native sequences. Useful DNA sequences include those sequences which hybridize under stringent hybridization conditions [see, T. Maniatis et al, *Molecular Cloning (A Laboratory Manual)*, Cold Spring Harbor Laboratory (1982), pages 387 to 389] to the DNA sequences. An example of one such stringent hybridization condition is hybridization at 4×SSC at 65° C., followed by a washing in 0.1×SSC at 65° C. for an hour. Alternatively an exemplary stringent hybridization condition is in 50% formamide, 4×SSC at 42° C. Preferably, these hybridizing DNA sequences are at least about 18 nucleotides in length, i.e., about the size of a CDR.

V. Fusion Molecules and Fusion Proteins

Fusion molecules can encode fusion proteins which includes engineered antibodies such as, chimeric antibodies, and humanized antibodies. A desired fusion molecule contains CDR sequences encoding peptides having the antigen specificity of an IL4 antibody, preferably a high affinity antibody such as is provided by the present invention inserted into a first fusion partner (a human framework or human immunoglobulin variable region).

Preferably, the first fusion partner is operatively linked to a second fusion partner. The second fusion partner is defined above, and may include a sequence encoding a second antibody region of interest, for example an Fc region. Second fusion partners may also include sequences encoding another immunoglobulins to which the light or heavy chain constant region is fused in frame or by means of a linker sequence. Engineered antibodies directed against functional fragments or analogs of IL4 may be designed to elicit enhanced binding with the same antibody.

The second fusion partner may also be associated with effector agents as defined above, including non-protein carrier molecules, to which the second fusion partner may be operatively linked by conventional means.

Fusion or linkage between the second fusion partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde, and the like. Such techniques are known in the art and readily described in conventional chemistry and biochemistry texts.

Additionally, conventional linker sequences which simply provide for a desired amount of space between the second fusion partner and the effector agent may also be constructed into the fusion molecule. The design of such linkers is well known to those of skill in the art.

In addition, signal sequences for the molecules of the invention may be modified to enhance expression. As one example a desired fusion protein having an amino acid sequence of the murine heavy chain sequence, which is identical to the chimeric variable heavy chain ($V_H$) of FIG. 2 [SEQ ID NO: 4], had the original signal peptide replaced with another signal sequence (amino acid residues 1-20) [SEQ ID NO: 6].

An exemplary fusion protein contains a variable heavy and/or light chain peptide or protein sequence having the antigen specificity of MAb 3B9, e.g., the $V_H$ [amino acid residues 21-141 of SEQ ID NO: 9 and 10] and $V_L$ chains [amino acid residues 21-132 of SEQ ID NOS: 1 and 2]. Still another desirable fusion protein of this invention is characterized by the amino acid sequence containing at least one, and preferably all of the CDRs of the variable region of the heavy and/or light chains of the murine antibody molecule 3B9 with the remaining sequences being derived from a human source, or a functional fragment or analog thereof. See, e.g., the humanized $V_H$ and $V_L$ regions of SEQ ID NOS: 11 and 12 and SEQ ID NOS: 13 and 14 (FIGS. 4 and 5).

In still a further embodiment, the engineered antibody of the invention may have attached to it an additional agent. For example, the procedure of recombinant DNA technology may be used to produce an engineered antibody of the invention in which the Fc fragment or CH3 domain of a complete antibody molecule has been replaced by an enzyme or other detectable molecule. (i.e., a polypeptide effector or reporter molecule)

The second fusion partner may also be operatively linked to a non-immunoglobulin peptide, protein or fragment thereof heterologous to the CDR-containing sequence having the antigen specificity of murine 3B9. The resulting protein may exhibit both anti-IL4 antigen specificity and characteristics of the non-immunoglobulin upon expression. That fusion partner characteristic may be, e.g., a functional characteristic such as another binding or receptor domain, or a therapeutic characteristic if the fusion partner is itself a therapeutic protein, or additional antigenic characteristics.

Another desirable protein of this invention may comprise a complete antibody molecule, having full length heavy and light chains, or any discrete fragment thereof, such as the Fab or F(ab')$_2$ fragments, a heavy chain dimer, or any minimal recombinant fragments thereof such as an F$_v$ or a single-chain antibody (SCA) or any other molecule with the same specificity as the selected donor MAb, e.g., MAb3B9 or 6A1. Such protein may be used in the form of a fusion protein, or may be used in its unfused form.

Whenever the second fusion partner is derived from another antibody, e.g., any isotype or class of immunoglobulin framework or constant region, an engineered antibody results. Engineered antibodies can comprise immunoglobulin (Ig) constant regions and variable framework regions from one source, e.g., the acceptor antibody, and one or more (preferably all) CDRs from the donor antibody, e.g., the anti-IL4 antibody described herein. In addition, alterations, e.g., deletions, substitutions, or additions, of the acceptor MAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of the IL4 MAb (optionally modified as described) or one or more of the below-identified heavy or light chain CDRs (see Example 3). The engineered antibodies of the invention are neutralizing, i.e., they desirably block binding to the receptor of the IL4 protein. For example, the engineered antibody derived from MAb 3B9 is directed against a specific tertiary protein epitope of human IL4 believed to be at the B-C loop→C helix region, as described above.

Such engineered antibodies may include a humanized antibody containing the framework regions of a selected human immunoglobulin or subtype, or a chimeric antibody containing the human heavy and light chain constant regions fused to the IL4 antibody functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody.

Desirably the heterologous framework and constant regions are selected from human immunoglobulin classes and isotypes, such as IgG (subtypes 1 through 4), IgM, IgA, and IgE. However, the acceptor antibody need not comprise only human immunoglobulin protein sequences. For instance a gene may be constructed in which a DNA sequence encoding part of a human immunoglobulin chain is fused to a DNA sequence encoding a non-immunoglobulin amino acid sequence such as a polypeptide effector or reporter molecule.

One example of a particularly desirable humanized antibody contains CDRs of 3B9 inserted onto the framework regions of a selected human antibody sequence. For neutralizing humanized antibodies one, two or preferably three CDRs from the IL4 antibody heavy chain and/or light chain variable regions are inserted into the framework regions of the selected human antibody sequence, replacing the native CDRs of the latter antibody.

Preferably, in a humanized antibody, the variable domains in both human heavy and light chains have been engineered by one or more CDR replacements. It is possible to use all six CDRs, or various combinations of less than the six CDRs. Preferably all six CDRs are replaced. It is possible to replace the CDRs only in the human heavy chain, using as light chain the unmodified light chain from the human acceptor antibody. Still alternatively, a compatible light chain may be selected from another human antibody by recourse to the conventional antibody databases. The remainder of the engineered antibody may be derived from any suitable acceptor human immunoglobulin.

The engineered humanized antibody thus preferably has the structure of a natural human antibody or a fragment thereof, and possesses the combination of properties required for effective therapeutic use, e.g., treatment of IL4 mediated inflammatory diseases in man, or for diagnostic uses.

As another example, an engineered antibody may contain three CDRs of the variable light chain region of 3B9 [SEQ ID NO: 16, 18, 20 and 28] and three CDRs of the variable heavy chain region of 3B9 [SEQ ID NO: 22, 24 and 26]. The resulting humanized antibody is characterized by the antigen binding specificity and high affinity of MAb 3B9.

It will be understood by those skilled in the art that an engineered antibody may be further modified by changes in variable domain amino acids without necessarily affecting the specificity and high affinity of the donor antibody (i.e., an analog). For example, humanized monoclonal antibodies have been constructed wherein the light chain amino acid residue at position 120 was an arginine [SEQ ID NO:13 and 14] or threonine [SEQ ID NOS:57 and 58]. It is anticipated that heavy and light chain amino acids may be substituted by other amino acids either in the variable domain frameworks or CDRs or both.

In addition, the constant region may be altered to enhance or decrease selective properties of the molecules of the instant invention. For example, dimerization, binding to Fc receptors, or the ability to bind and activate complement (see, e.g., Angal et al., *Mol. Immunnol*, 30:105-108 (1993), Xu et al., *J. Biol. Chem*, 269:3469-3474 (1994), Winter et al., EP 307, 434-B).

A fusion protein which is a chimeric antibody differs from the humanized antibodies described above by providing the entire non-human donor antibody heavy chain and light chain variable regions, including framework regions, in association with human immunoglobulin constant regions for both chains. It is anticipated that chimeric antibodies which retain additional non-human sequence relative to humanized antibodies of this invention may elicit a significant immune response in humans.

Such antibodies are useful in the prevention and treatment of IL4 mediated allergic disorders, as discussed below.

VI. Production of Fusion Proteins and Engineered Antibodies

Preferably, the variable light and/or heavy chain sequences and the CDRs of MAb 3B9 [SEQ ID NO: 16, 18, 20, 22, 24 and 26] or other suitable donor MAbs (e.g., 6A1), and their encoding nucleic acid sequences, are utilized in the construction of fusion proteins and engineered antibodies, preferably humanized antibodies, of this invention, by the following process. The same or similar techniques may also be employed to generate other embodiments of this invention.

A hybridoma producing a selected donor MAb, e.g., the murine antibody 3B9, is conventionally cloned, and the DNA of its heavy and light chain variable regions obtained by techniques known to one of skill in the art, e.g., the techniques described in Sambrook et al., *Molecular Cloning (A Laboratory Manual)*, 2nd edition, Cold Spring Harbor Laboratory (1989). The variable heavy and light regions of 3B9 containing at least the CDRs and those portions of the acceptor MAb light and/or heavy variable domain framework region required in order to retain donor MAb binding specificity, as well as the remaining immunoglobulin-derived parts of the antibody chain derived from a human immunoglobulin are obtained using polynucleotide primers and reverse transcriptase. The CDRs are identified using a known database and by comparison to other antibodies.

A mouse/human chimeric antibody may then be prepared and assayed for binding ability. Such a chimeric antibody contains the entire non-human donor antibody $V_H$ and $V_L$ regions, in association with human Ig constant regions for both chains.

Homologous framework regions of a heavy chain variable region from a human antibody were identified using computerized databases, e.g., KABAT®, and a human antibody having homology to 3B9 was selected as the acceptor antibody. The sequences of synthetic heavy chain variable regions containing the 3B9 CDRs within the human antibody frameworks were designed with optional nucleotide replacements in the framework regions to incorporate restriction sites. This designed sequence is then synthesized by overlapping oligonucleotides, amplified by polymerase chain reaction (PCR), and corrected for errors.

A suitable light chain variable framework region was designed in a similar manner.

A humanized antibody may be derived from the chimeric antibody, or preferably, made synthetically by inserting the donor MAb CDRs from the heavy and light chains appropriately within the selected heavy and light chain framework. Alternatively, a humanized antibody of the invention made be prepared using standard mutagenesis techniques. Thus, the resulting humanized antibody contains human framework regions and donor MAb CDRs. There may be subsequent manipulation of framework residues. The resulting humanized antibody can be expressed in recombinant host cells, e.g., COS or CHO cells. Additional details of this procedure are provided in Example 4. Other humanized antibodies may be prepared using this technique on other suitable IL4-specific, neutralizing, high titer, non-human antibodies.

A conventional expression vector or recombinant plasmid is produced by placing these coding sequences for the fusion protein in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector is produced having a DNA sequence which encodes a complementary antibody light or heavy chain. Preferably this second expression vector is identical to the first except insofar as the coding sequences and selectable markers are concerned so to ensure as far as possible that each polypeptide chain is functionally expressed.

A selected host cell is co-transfected by conventional techniques with both the first and second vectors or simply transfected by a single vector to create the transfected host cell of the invention comprising both the recombinant or synthetic light and heavy chains. The transfected cell is then cultured by conventional techniques to produce the engineered antibody of the invention. The humanized antibody which includes the association of both the recombinant heavy chain and/or light chain is screened from culture by appropriate assay, such as ELISA or RIA. Similar conventional techniques may be employed to construct other fusion proteins and molecules of this invention.

Suitable vectors for the cloning and subcloning steps employed in the methods and construction of the compositions of this invention may be selected by one of skill in the art. For example, the conventional pUC series of cloning vectors, may be used. One vector used is pUC19, which is commercially available from supply houses, such as Amersham (Buckinghamshire, United Kingdom) or Pharmacia (Uppsala, Sweden). Additionally, any vector which is capable of replicating readily, has an abundance of cloning sites and marker genes, and is easily manipulated may be used for cloning. Thus, the selection of the cloning vector is not a limiting factor in this invention.

Similarly, the vectors employed for expression of the engineered antibodies according to this invention may be selected by one of skill in the art from any conventional vector. The vectors also contain selected regulatory sequences which are in operative association with the DNA coding sequences of the immunoglobulin regions and capable of directing the replication and expression of heterologous DNA sequences in selected host cells, such as CMV promoters. These vectors contain the above described DNA sequences which code for the engineered antibody or fusion molecule. Alternatively, the vectors may incorporate the selected immunoglobulin sequences modified by the insertion of desirable restriction sites for ready manipulation.

The expression vectors may also be characterized by marker genes suitable for amplifying expression of the heterologous DNA sequences, e.g., the mammalian dihydrofolate reductase gene (DHFR) or neomycin resistance gene ($neo^R$). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the engineered antibodies or fusion molecules hereof. Host cells useful for the cloning and other manipulations of these cloning vectors are also conventional. However, most desirably, cells from various strains of *E. coli* are used for replication of the cloning vectors and other steps in the construction of fusion proteins of this invention.

Suitable host cells or cell lines for the expression of the engineered antibody or fusion protein of the invention are preferably a eukaryotic cell such as CHO, COS, a fibroblast cell (e.g. 3T3), and myeloid cells among others, and most preferably a mammalian cell, such as a CHO cell or a myeloid cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant MAbs of the present invention. However, due to the tendency of proteins expressed in bacterial cells to be in an unfolded or improperly folded form or in a non-glycosylated form, any recombinant MAb produced in a bacterial cell would have to be screened for retention of antigen binding ability. If the molecule expressed by the bacterial cell was produced in a properly folded form, that bacterial cell would be a desirable host. For example, various strains of E. coli used for expression are well-known as host cells in the field of biotechnology. Various strains of B. subtilis, Streptomyces, other bacilli and the like may also be employed in this method.

Where desired, strains of yeast cells known to those skilled in the art are also available as host cells, as well as insect cells, e.g. Drosophila and Lepidoptera and viral expression systems. See, e.g. Miller et al., Genetic Engineering, 8:277-298, Plenum Press (1986) and references cited therein.

The general methods by which the vectors of the invention may be constructed, transfection methods required to produce the host cells of the invention, and culture methods necessary to produce the fusion protein or engineered antibody of the invention from such host cell are all conventional techniques. Likewise, once produced, the fusion proteins or engineered antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention.

Yet another method of expression of the humanized antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

Once expressed by the desired method, the engineered antibody is then examined for in vitro activity by use of an appropriate assay. Presently conventional ELISA assay formats are employed to assess qualitative and quantitative binding of the engineered antibody to an IL4 epitope. Additionally, other in vitro assays, e.g. BIAcore [Pharmacia], may also be used to verify neutralizing efficacy prior to subsequent human clinical studies performed to evaluate the persistence of the engineered antibody in the body despite the usual clearance mechanisms.

Following the procedures described for humanized antibodies prepared from 3B9, one of skill in the art may also construct humanized antibodies from other donor IL4 antibodies, variable region sequences and CDR peptides described herein. Engineered antibodies can be produced with variable region frameworks potentially recognized as "self" by recipients of the engineered antibody. Minor modifications to the variable region frameworks can be implemented to effect large increases in antigen binding without appreciable increased immunogenicity for the recipient. Such engineered antibodies can effectively treat a human for IL4 mediated conditions. Such antibodies may also be useful in the diagnosis of such conditions.

VII. Therapeutic/Prophylactic Uses

This invention also relates to a method of treating humans experiencing an allergic disorder which comprises administering an effective dose of antibodies including one or more of the engineered antibodies or fusion proteins described herein, or fragments thereof.

The therapeutic response induced by the use of the molecules of this invention is produced by the binding to human IL4 and thus subsequently blocking IgE release. Thus, the molecules of the present invention, when in preparations and formulations appropriate for therapeutic use, are highly desirable for those persons experiencing an allergic response, such as an allergic rhinitis, conjunctivitis, atopic dermatitis, atopic asthma, and anaphylactic shock.

The fusion proteins, antibodies, engineered antibodies or fragments thereof of this invention may also be used in conjunction with other antibodies, particularly human MAbs reactive with other markers (epitopes) responsible for the condition against which the engineered antibody of the invention is directed. Similarly MAbs reactive with epitopes responsible for the condition in a selected animal against which the antibody of the invention is directed may also be employed in veterinary compositions.

The therapeutic agents of this invention are believed to be desirable for treatment of allergic conditions for from about 2 days to about 3 weeks, or as needed. For example, longer treatments may be desirable when treating seasonal rhinitis or the like. This represents a considerable advance over the currently used infusion protocol with prior art treatments of IL4 mediated disorders. The dose and duration of treatment relates to the relative duration of the molecules of the present invention in the human circulation, and can be adjusted by one of skill in the art depending upon the condition being treated and the general health of the patient.

The mode of administration of the therapeutic agent of the invention may be any suitable route which delivers the agent to the host. The fusion proteins, antibodies, engineered antibodies, and fragments thereof, and pharmaceutical compositions of the invention are particularly useful for parenteral administration, i.e., subcutaneously, intramuscularly, intravenously, or intranasally.

Therapeutic agents of the invention may be prepared as pharmaceutical compositions containing an effective amount of the engineered (e.g., humanized) antibody of the invention as an active ingredient in a pharmaceutically acceptable carrier. In the prophylactic agent of the invention, an aqueous suspension or solution containing the engineered antibody, preferably buffered at physiological pH, in a form ready for injection is preferred. The compositions for parenteral administration will commonly comprise a solution of the engineered antibody of the invention or a cocktail thereof dissolved in an pharmaceutically acceptable carrier, preferably an aqueous carrier. A variety of aqueous carriers may be employed, e.g., 0.4% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an engineered antibody of the invention. Similarly, a pharmaceutical composition of the invention for intravenous infusion could be made up to contain about 250 ml of sterile Ringer's solution, and about 1 to about 30 and preferably 5 mg to about 25 mg of an engineered antibody of the invention. Actual methods for preparing parenterally administrable compositions are well known or will be apparent to those skilled in the art and are described in more detail in, for example, Remington's Pharmaceutical Science, 15th ed., Mack Publishing Company, Easton, Pa.

It is preferred that the therapeutic agent of the invention, when in a pharmaceutical preparation, be present in unit dose forms. The appropriate therapeutically effective dose can be determined readily by those of skill in the art. To effectively treat an inflammatory disorder in a human or other animal, one dose of approximately 0.1 mg to approximately 20 mg per 70 kg body weight of a protein or an antibody of this invention should be administered parenterally, preferably i.m. (intramuscularly). Such dose may, if necessary, be repeated at appropriate time intervals selected as appropriate by a physician during the inflammatory response.

The invention also encompasses the administration of the IL4 fusion proteins of this invention concurrently or sequentially with other antibodies or fusion proteins characterized by anti-IL4 activity, such as anti-tumor necrosis factor activity or other pharmaceutical activities compatible with the IL4 receptor binding ability of the fusion proteins of this invention. Such other antibodies are available commercially or can be designed in a manner similar to that described herein.

The fusion proteins and engineered antibodies of this invention may also be used in diagnostic regimens, such as for the determination of IL4 mediated disorders or tracking progress of treatment of such disorders. As diagnostic reagents, these fusion proteins may be conventionally labelled for use in ELISA's and other conventional assay formats for the measurement of IL4 levels in serum, plasma or other appropriate tissue. The nature of the assay in which the fusion proteins are used are conventional and do not limit this disclosure.

The antibodies, engineered antibodies or fragments thereof described herein can be lyophilized for storage and reconstituted in a suitable carrier prior to use. This technique has been shown to be effective with conventional immunoglobulins and art-known lyophilization and reconstitution techniques can be employed.

The following examples illustrate various aspects of this invention including the construction of exemplary engineered antibodies and expression thereof in suitable vectors and host cells, and are not to be construed as limiting the scope of this invention. All amino acids are identified by conventional three letter or single letter codes. All necessary restriction enzymes, plasmids, and other reagents and materials were obtained from commercial sources unless otherwise indicated. All general cloning ligation and other recombinant DNA methodology were as performed in T. Maniatis et al., cited above, or the second edition thereof (1989), eds. Sambrook et al., by the same publisher ("Sambrook et al.").

EXAMPLE 1

Production of MAb 3B9

A. Immunization Procedure

Four mice (F1 hybrids of Balb/c and C57BL/6) were immunized subcutaneously with 50 µg recombinant *E. coli* human IL4 in Freunds complete adjuvant and 4 weeks later boosted intraperitoneally (i.p.) with 50 µg IL4 in Freunds incomplete adjuvant. On the basis of a good serum antibody titre to IL4 one mouse received further immunizations of 200 µg IL4 (i.p. in saline) at 8 weeks, two days later with 100 µg IL4 (i.p. in saline) and two days later with 50 µg IL4 (i.p. in saline). Two days following the final immunization a splenectomy was performed.

B. Fusion Procedure and Screening System

Mouse spleen cells were used to prepare hydridomas (by standard procedures, e.g. as described by Kohler et al, *Nature*, 256:495 (1975)) from which >250 clones of cells were screened for secretion of antibody to IL4, using the commercially available BLAcore system, and ELISA assays as described below, for IL4 binding. Five wells gave a positive response. Only 1 clone from mice, 3B9, was strongly positive. All secondary clones derived from 3B9 were positive.

EXAMPLE 2

ELISA Assays and Affinity Constants

A. ELISA

The screening assay, performed as follows, was designed to measure affinity for native human IL4. For experiment 1 aldehyde activated 96-well plates were coated with IL4 at 1 µg/mL, 100 µl/well in 0.1 M borate buffer, pH 8.5, and incubated overnight at RT. The hIL4 was covalently attached to the plate. IL4 solution was aspirated and non-specific binding (NSB) sites were blocked with 1% bovine serum albumin (BSA) in TBS buffer (50 mM Tris, 150 mM NaCl, 1 mM $MgCl_2$, 0.02% $NaN_3$, pH 7.4) for 60 minutes at 37° C. Following this and each of the following steps, the plate was washed 4 times in wash buffer (10 mM Tris, 150 mM NaCl, 0.05% Tween 20, 0.02% $NaN_3$, pH 7.4). Following this, 50 µL hybridoma medium (or purified 3B9 or Fab fragments) and 50 µL assay buffer (0.5% bovine gamma globulin in TBS buffer) was added and the plates were incubated for 60 minutes at 37° C. One hundred µL of biotinylated anti-mouse antibody was added per well in assay buffer and incubated as above. One hundred µL of alkaline phosphatase conjugated streptavidin was added per well and incubated (30 minutes at 37° C.). One hundred µL/well PNP substrate was added and incubated 30 minutes at 37° C. Readings were taken at an optical density of 405 nm.

For experiment 2, streptavidin-coated plates (100 µL/well, 1 µg/mL in phosphate buffered saline (PBS)) were incubated overnight at 4° C. and were assayed as follows. Streptavidin solution was aspirated, NSB sites blocked with 1% BSA in TBS buffer (60 minutes at 37° C.). Following this step, and each of the steps which follow, the plates were washed four times in wash buffer. Fifty µL biotinylated IL4 was added with 50 µL assay buffer and incubated for 30 minutes at 37° C. Following this, 50 µL purified 3B9 IgG or Fab fragment (or hybridoma medium) plus 50 µL assay buffer was added, incubated 60 minutes at 37° C. One hundred µL anti-mouse IgG alkaline phosphatase conjugate was added and incubated for 60 minutes at 37° C. One hundred µL PNP substrate was added and incubated 30 minutes at 37° C. The readings were taken as above.

B. Calculation of 3B9 Affinity for IL-4

Using the results of the experiments described above, and summarized as follows, the $K_d$ for 3B9 was calculated as described in Beatty et al, *J. Immunol. Methods*, 100:173-179 (1987):

$$K_{\mathit{aff}} = \frac{1}{2(2[Ab^*] - [Ab])}$$

Ab*=concentration of Ab bound at 150 ng/ml biotinylated hIL4

Ab=concentration of Ab bound at 300 ng/ml biotinylated hIL4

Dissociation constants, $K_d$, were calculated from the relationship:

$$K_d = \frac{1}{K_{\mathit{aff}}}$$

Experiment 1: ELISA assay on a streptavidin coated 96-well plate (100 ng/well). $K_d$=2.2×10$^{-10}$ M (3B9 Fab)

Experiment 2: ELISA assay on a streptavidin coated 96-well plate (100 ng/well). $K_d$=1.4×10$^{-10}$ M (3B9 IgG)

C. Specificity

MAb 3B9 recognizes human IL4, but does not recognize bovine or murine IL4. One way to determine this is as follows. An ELISA can be performed using a 96 well plate coated with anti-mouse IgG, and subsequently blocked with bovine serum albumin, upon which 50 μL 3B9 (100 ng/mL), 25 μL of non-human IL4, and 25 μL biotin-IL4 were incubated for 60 minutes at 37° C., followed by a wash, streptavidin conjugated alkaline phosphatase and PNP.

Similarly, MAb 6A1 was found not to recognize bovine or murine IL4.

EXAMPLE 3

Humanized Antibody

One humanized antibody was designed to contain murine CDRs within a human antibody framework. This humanized version of the IL4 specific mouse antibody 3B9, was prepared by performing the following manipulations.

A. cDNA Cloning cDNA clones were made of the 3B9 heavy and light chains from mRNA extracted out of the 3B9 hybridoma cell line [Example 1] using a Boehringer Mannheim kit. Primers specific for either the mouse hinge region or kappa constant region were used for first strand synthesis.

The kappa chain primer is [SEQ ID NO: 29]:

5'-CTAACACTCATTCCTGTTGAAGCTCTTGACAATGGG-3'

The gamma heavy chain primer is [SEQ ID NO: 30]:

5'GTACATATGCAAGGCTTACAACCACAATC 3'.

The double stranded cDNA was cloned directly into plasmids pGEM7f+[Promega] that were then transformed into *E. coli* DH5-α [Bethesda Research Labs].

B. DNA Sequencing

Eight heavy and one light chain murine cDNA clones from Part A above were sequenced. The results of sequencing of the variable regions of these clones are shown in SEQ ID NO: 1 and 2 and 3 and 4. Each clone contained amino acids known to be conserved among mouse heavy chain variable regions or light chain variable regions, and murine signal sequences. The CDR amino acid sequences are listed below.

The CDR regions for the heavy chain are SEQ ID NO: 22, 24 and 26, (amino acids 50-56, 71-86 and 119-129 of SEQ ID NO: 4). See FIG. 2. These sequences are encoded by SEQ ID NO: 21, SEQ ID NO: 23, and SEQ ID NO: 25, respectively. The CDR regions for the light chain are SEQ ID NO: 16, 18 and 20 (amino acids 45-58, 74-80, and 113-121 of SEQ ID NO: 2). See FIG. 1. These sequences are encoded by SEQ ID NO: 15, 17, and 19, respectively.

C. Selection of Human Frameworks

Following the cloning of 3B9, the amino acid sequences of the variable region (amino acids 21-132 of SEQ ID NO: 2 and amino acids 20 to 140 of SEQ ID NO: 4) were compared with the human immunoglobulin sequence database using the KABAT® and the SWISS databases in order to identify a human framework for both the heavy and light chains which would most closely match the murine parent in sequence homology. In addition to these searches for sequence homology, the heavy and light chains were also evaluated against a positional database generated from structural models of the Fab domain to assess potential conflicts due to amino acid substitutions which might influence CDR presentation. For the present case, no obvious conflicts were detected in the structural search; hence, the DNA coding deduced from the amino acid sequence homology searches was used.

The heavy chain framework regions of an antibody obtained from a human myeloma immunoglobulin (COR) was used [E. M. Press and N. M. Hogg, *Biochem. J.*, 117:641-660 (1970)]. This sequence was found to be approximately 77% homologous (69.4% identity) to the 3B9 variable chain region at the amino acid level.

For a suitable light chain variable framework region, the light chain variable framework sequence of the human antibody identified in H. G. Klobeck et al, *Nucl. Acids Res.*, 13:6515-6529 (1985) was used. The human antibody sequence was found to be approximately 80.2% homologous (72.0% identity) to the murine 3B9 variable light chain region at the amino acid level.

Given the murine 3B9 CDRs [SEQ ID NO: 15-26] and the sequence of the human antibody, a synthetic heavy chain was made and PCR performed to fill in and amplify the DNA. These sequences were synthesized by the following overlapping oligonucleotides and amplified by PCR. SEQ ID NO: 31-37 provides five overlapping oligos and 2 PCR primers. Oligo 1 [SEQ ID NO: 31] is found spanning bases 5-121. Oligo 2 [SEQ ID NO: 32] is found spanning bases 122-241, and oligo 3 [SEQ ID NO: 33] is found spanning bases 242-361. The two bottom strand primers SEQ ID NO: 34 and SEQ ID NO: 35 span bases 134-110 and bases 253-230. Any errors in the mapped sequence which were inserted by PCR were corrected. PCR was again performed using as the 5' primer nucleotides 1-25 SEQ ID NO: 36 and as the 3' primer nucleotides 361-341 SEQ ID NO: 37.

Figure 9:
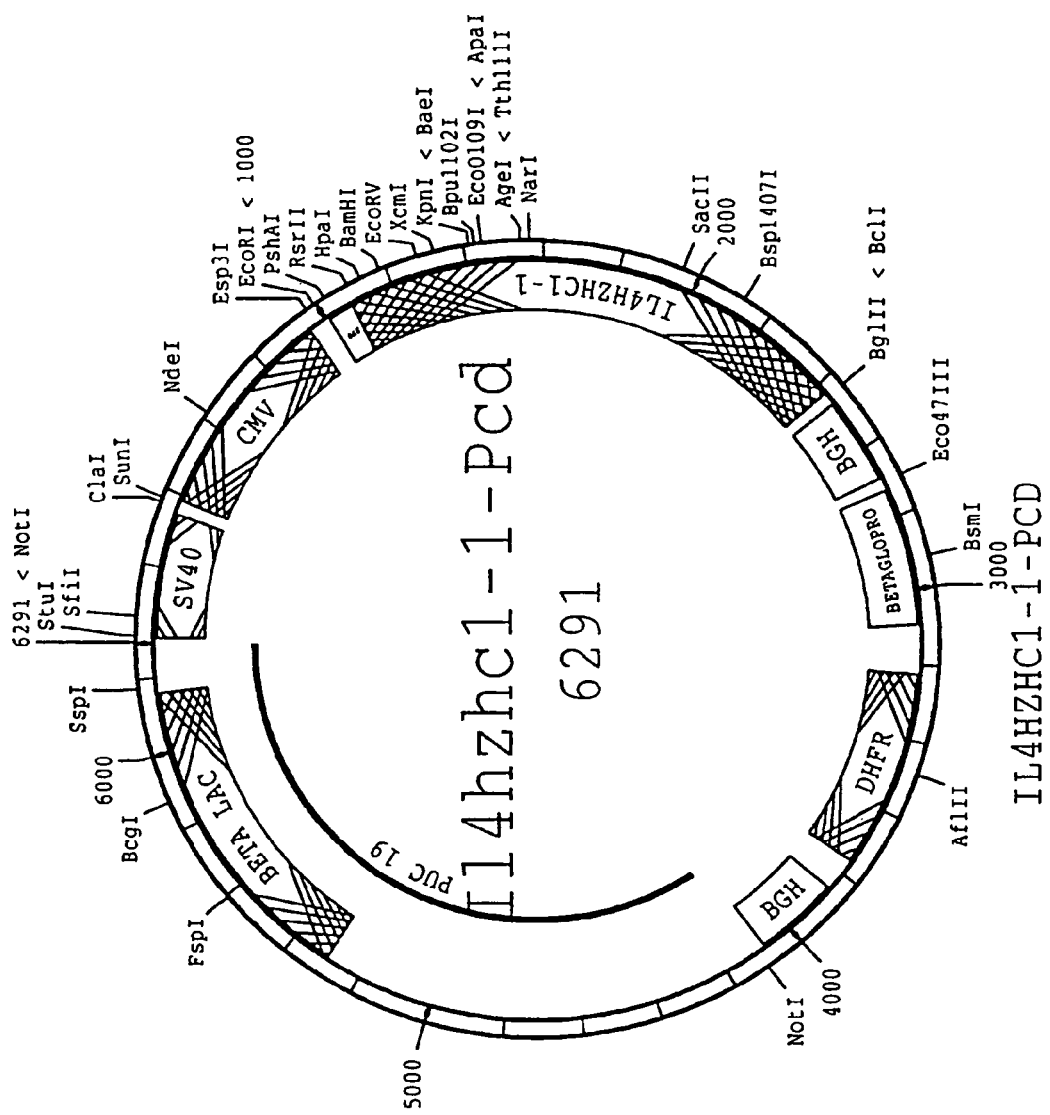
FIG. 9 is a schematic drawing of plasmid pIL4hzhc-1-pcd employed to express the synthetic IL4 heavy chain variable region of SEQ ID NOS: 11 and 12 in mammalian cells. The plasmid differs from that of FIG. 7 by containing a humanized heavy chain variable region rather than that of the chimeric heavy chain.

The synthetic variable region was ligated into the expression vector pCD along with the synthetic signal sequence SEQ ID NO: 5 and 6 from the chimeric heavy chain construction along with an IgG, human constant region. The synthetic $V_H$ and signal sequence nucleotide and amino acid sequences are provided in FIG. 4 [SEQ ID NOS: 11 and 12]. The amino acid sequences of the CDRs [SEQ ID NOS: 22, 24 and 26] are identical to the murine 3B9 CDRS. However, the coding sequences for these CDRs [SEQ ID NOS: 54, 55 and 56] differ from the murine 3B9 coding sequences [SEQ ID NOS: 21, 23 and 25]. The resulting expression vector, IL4hzhc1-1-Pcd is shown in FIG. 9.

The CDR gene regions of a pre-existing light chain framework were restriction digest removed and replaced with the following synthetic IL-4 CDR genes, which were synthetically made.

```
For CDR 1:
SEQ ID NO: 38:
5'CTAGCTGTGTCTCTGGGCGAGAGGGCCACCATCAACTGCAAGG 3'

SEQ ID NO: 39:
CCTTGCAGTTGATGGTGGCCCTCTCGCCCAGAGACACAG

SEQ ID NO: 40:
TCGAGAGGCCTCCCAAAGTGTTGATTATGATGGTGATAGTTATATGAACT
GGTATCAGCAGAAACCC

SEQ ID NO: 41:
GGGTTTCTGCTGATACCAGTTCATATAACTATCACCATCATAATCAACAC
TTTGGGAGGCCTC

For CDR2:
SEQ ID NO: 44:
GGGCAGCCTCCTAAGTTGCTCATTTACGCTGCATCCAATCTAGAATCTGG
GGTAC

SEQ ID NO: 45:
CCCAGATTCTAGATTGGATGCAGCGTAAATGAGCAACTTAGGAGGCTGCC
C

For CDR3:
SEQ ID NO: 42:
ATACTACTGTCAGCAAAGTAATGAGGATCCTCCGAGGTTCGGCGGAGGGA
C

SEQ ID NO: 43:
CTTGGTCCCTCCGCCGAACCTCGGAGGATCCTCATTACTTTGCTGACAGT
AGT
```

Figure 10:
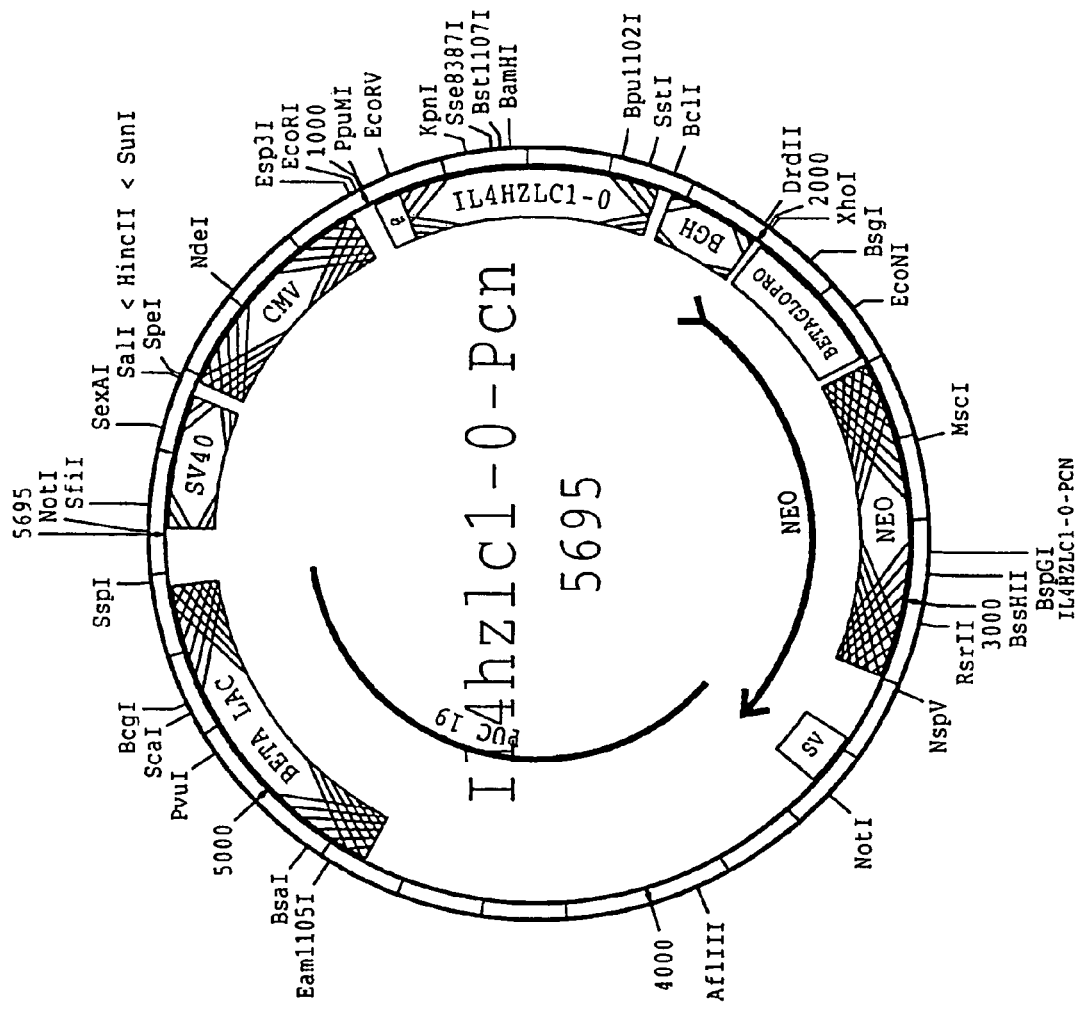
FIG. 10 is a schematic drawing of plasmid pIL4hzlc1-0-Pcn employed to express the humanized IL4 light chain variable region of SEQ ID NOS: 13 and 14 in mammalian cells. The plasmid differs from that of FIG. 8 by containing a humanized light chain variable region rather than that of the chimeric light chain and does not encode the DHFR gene.

The synthetic $V_L$ and signal sequence nucleotide and amino acid sequences are provided in FIG. 5 [SEQ ID NOS: 13 and 14]. The amino acid sequences of the first two CDRs [SEQ ID NOS: 16 and 18] are identical to the corresponding murine 3B9 CDRs. However, the coding sequence for the first CDR [SEQ ID NO: 53] differs from the murine 3B9 coding sequence [SEQ ID NO: 15]. Further, in the last CDR, two humanized constructs of the 3B9 amino acid sequence were constructed. One, [SEQ ID NO: 28], differs by a single amino acid [SEQ ID NO: 20] from the native murine 3B9 sequence. SEQ ID NO: 28 is encoded by SEQ ID NO: 27. The synthetic variable light regions were ligated into the expression vector along with the signal sequence [SEQ ID NOS: 7 and 8]. One of the resulting expression vectors, IL4hzlc1-O-Pcn is illustrated in FIG. 10.

These synthetic variable light and/or heavy chain sequences are employed in the construction of a humanized antibody.

EXAMPLE 4

Expression of Humanized MAb in COS and CHO cells pUC18 subclones for the $V_H$ were made to add a signal sequence originally obtained from a human antibody SEQ ID NO: 5. For the $V_L$, pUC18 subclones were made to add a signal sequence SEQ ID NO: 7.

The humanized heavy chain, derived from an $IgG_1$ isotype, exhibits 89.3% homology (84.3% identity) at the amino acid level with the murine heavy chain from 3B9. This synthetic $V_H$ is provided in amino acids 20-141 of SEQ ID NOS: 11 and 12.

The humanized light chain, a human kappa chain, shows 92.0% homology (86.6% identity) with 3B9 at the amino acid level. This synthetic $V_L$ [amino acids 21 to 131 of SEQ ID NOS: 13 and 14] containing the 3B9 CDRs was designed and synthesized as described above for the synthetic heavy chains.

The DNA fragments containing their respective signal linked to either the humanized heavy or light variable regions were inserted into pUC19-based mammalian cell expression plasmids containing CMV promoters and the human heavy chain or human light chain constant regions of the chimera produced in Example 5 below, by conventional methods [Maniatis et al., cited above] to yield the plasmids IL4hzhc1-1Pcd (heavy chain) [FIG. 9] and IL4hzlc1-o-Pcn)(light chain) [FIG. 10]. The HZHC and HZLC plasmids are co-transfected into COS cells and supernatants assayed by the ELISA described immediately above for the presence of humanized antibody after three and five days. Another humanized antibody was constructed but with an IgG4 isotype.

The above example describes the preparation of an exemplary engineered antibody. Similar procedures may be followed for the development of other engineered antibodies, using other anti-IL4 antibodies (e.g., 6A1—Example 7) developed by conventional means.

EXAMPLE 5

Construction of Chimeric Antibody

A. A chimeric heavy chain was constructed by isolating the murine variable heavy chain region from the original mouse MAb 3B9 as an EcoRI-BstEII restriction fragment. A small DNA oligomer was designed and synthesized to link the mouse variable region with the human IgG1 constant region (BstEII-ApaI):

```
5'primer: SEQ ID NO: 50:
GTCACCGTCTCCTCAGCTAGCACCAAGGGGC

3'primer: SEQ ID NO: 51:
CTTGGTGCTAGCTGAGGAGACG
```

These two fragments were ligated into plasmid pCD (See FIG. 7) (digested with EcoRI and Apa1) that already encodes the human IgG1 constant region. This clone did not express; therefore, the wild-type 5UTR and signal sequence were deleted and replaced with SEQ ID NO:5 and 6.

Because a convenient restriction endonuclease site was not available at the 3' end of the signal sequence, a BstEII site was introduced (i.e., a silent mutation) via PCR. The following PCR primers were used:

```
SEQ ID NO: 48: 5'primer: 5'CAGGTTACCCTGAAAGAGTC 3'

SEQ ID NO: 49: 3'primer: 5'GAAGTAGTCCTTGACCAG 3'
```

A BstEII-PstI restriction fragment was then isolated from this plasmid. A new signal sequence and 5'UTR were then designed and synthesized having EcoRI and BstEII ends.

```
SEQ ID NO: 46: 5'primer:  AATTCGAGGACGCCAGCAACATGGTG
                          TTGCAGACCCAGGTCTTCATTTCTCT
                          GTTGCTCTGGATCTCTGGTGCCTACG
                          GGCAG SEQ ID NO: 47: 3'primer:  GTAACCTGCCCGTAGGCACCAGAGAT
                          CCAGAGCAACAGAGAAATGAAGACCT
                          GGGTCTGCAACACCATGTTGCTGGCG
                          TCCTCG
```

Figure 8:
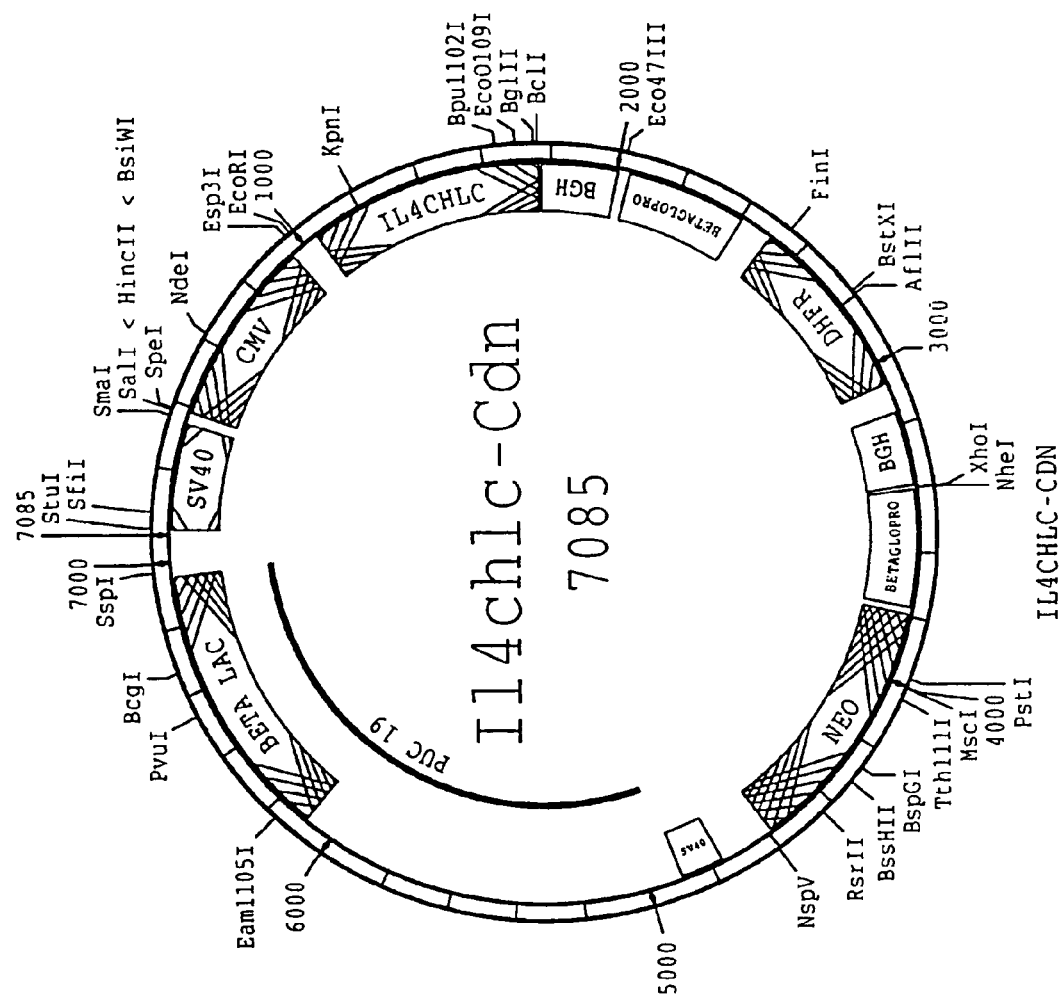
FIG. 8 is a schematic drawing of plasmid pIL4chlc-pcdn employed to express the chimeric IL4 light chain variable region of SEQ ID NOS: 1 and 2 in mammalian cells. The plasmid differs from that of FIG. 7 by containing a chimeric light chain variable region rather than that of the chimeric heavy chain, a human light chain constant region and a neomycin gene (Neo) in addition to DHFR.

The chimeric light chain was constructed by applying the PCR technique to the original murine 3B9 light chain that was cloned into pGEM72f(+) [Promega]. The primers utilized were the commercially available pUC18 universal reverse primer at the 5' end (EcoRI) and a 3' primer that introduces a NarI site [5'CATCTAGATGGCG CCGCCACAG-TACGTTTGATCTCCAGCTTGGTCCC3' SEQ ID NO: 52], used to fuse the mouse variable region to the human constant region. This variable region was then ligated into the expression vector pCDN (EcoRI NarI) (FIG. 8) that already contains the human kappa region.

Media supernatants were collected three and five days later and assayed by the ELISA described as follows: ELISA plates were coated with 0.1 µg of a goat antibody specific for the Fc region of human antibodies. The media supernatants were added for one hour. A horseradish peroxidase conjugated goat antibody specific for an entire human IgG antibody was added. This was followed by addition of ABTS peroxidase substrate (Kirkegaard & Perry Laboratories Inc., Gaithersburg, Md.) for one hour. Expression of the chimeric antibody was detected. In a second ELISA the COS cell supernatants containing the chimeric antibody bound specifically to recombinant human IL4 protein. This result confirmed that genes coding for an antibody specific for IL4 had been cloned.

B. A humanized heavy chain can also be obtained from this chimeric heavy chain. The humanized heavy chain was designed from by inserting the murine CDRs into a human framework. The chosen human framework was as described above, the most homologous protein sequence in the Swiss protein data based to the murine 3B9 $V_H$ (amino acids 20-140 of SEQ ID NO: 4). This humanized heavy chain sequence (EcoRI ApaI) was made synthetically and PCR performed to fill in and amplify DNA as described above. This synthetic variable region was ligated into the the expression vector pCD (EcoRI ApaI) together with the synthetic signal sequence SEQ ID NOS: 5 and 6 from the chimeric heavy chain construction and an $IgG_1$ human constant region.

Similarly, a humanized light chain can be derived from the chimeric light chain as described for the heavy chain. This gene (EcoRV NarI) was also made synthetically. The humanized $V_L$ was ligated into the expression vector pCN, digested with EcoRI NarI, along with a signal sequence (EcoRI EcoRV). The expression vector provided the human kappa constant region.

EXAMPLE 6

Purification and Thermodynamics—Humanized MAb

Purification of CHO expressed chimeric and humanized 3B9 can be achieved by conventional protein A (or G) affinity chromatography followed by ion exchange and molecular sieve chromatography. Similar processes have been successfully employed for the purification to >95% purity of other MAbs (e.g., to respiratory syncytial virus and malaria circumsporozoite antigens).

The affinity and detailed thermodynamics of IL4 binding to humanized MAb 3B9 and murine 3B9 (Example 1) were determined by titration microcalorimetry. This method measures binding reactions by virtue of their intrisic heats of reaction (see, e.g., Wiseman et al., Anal. Biochem, 179:131-137 (1989). The affinity of both MAbs was found to be too tight to measure directly at ambient temperature. Thus, a thermodynamic approach was taken: i) the affinity was measured at 60° C., where it is weak enough to be measured directly; and (ii) the temperature-dependence of the binding enthalpy was measured from 30-60° C. Together, these data allow calculation of the affinity over a wide range of temperatures using the Gibbs-Helmholz equation.

A summary of the IL4 binding thermodynamics of the humanized and murine 3B9 antibodies are presented in Table 1. Based upon the changes in free energy, enthalpy, entropy and heat capacity of the two MAbs, the binding thermodymanics are indistinguishable.

TABLE 1

Thermodynamics of hIL-4 binding to Humanzied 3B9 and Murine 3B9 at pH 7.4, 150 mM NaCl, and 25° C.

| mAb | $K_d$ pico-molar | $\Delta G$ kcal/ mol IL4 | $\Delta H$ kcal/ mol IL4 | $-T\Delta S$ kcal/ mol IL4 | $\Delta C$ cal/mol IL4/° K |
|---|---|---|---|---|---|
| humanized 3B9 | 11 | −13.6 ± 0.6 | −21.8 ± 2 | 8.2 ± 2.1 | −580 ± 160 |
| murine 3B9 | 19 | −13.3 ± 0.6 | −20.5 ± 1 | 7.2 ± 1.2 | −660 ± 200 |

IL4 affinities of humanzied 3B9 and murine 3B9 were measured in quadruplicate and duplicate, respectively.

EXAMPLE 7

Production and Characterization of Rat MAb

MAb 6A1, chosen for high affinity binding, was derived from an immunized rat, using the same immunization protocol as described for the mouse in Example 1. 6A1 was selected from hybridomas (specifically, hybridoma 3426A11C1B9) prepared from rats immunized with human IL4.

The $K_d$ for 6A1 was calculated as described in Beatty et al., J. Immunol. Methods, 100:173-179 (1987) to be $2 \times 10^{-10}$ M.

Hybridoma 3426A11C1B9 was deposited Oct. 6, 1993 with the European Collection of Animal Cell Cultures (ECACC), Public Health Laboratory Service Centre for Applied Microbiology & Research, Porton Down, Salisbury, Wiltshire, SP4 0JG, United Kingdom, under accession number 93100620, and has been accepted as a patent deposit, in accordance with the Budapest Treaty of 1977 governing the deposit of microorganisms for the purposes of patent procedure.

EXAMPLE 8

Biological Activity of MAbs: 3B9 (humanized). 3B9 (Murine) and 6A1

The following assays were performed using the procedures described below.

A. Binding to Glycosylated rhIL4

The above-identified antibodies were raised to non-glycosylated recombinant human IL4 (rhIL4) which was produced in E. coli. Because native human IL4 is glycosylated, it was important to confirm binding to material secreted by a mammalian cell line. 3B9 binds equally well to both glycosylated and non-glycosylated human recombinant IL4, and is not therefore directed to an epitope that would be masked on natural human IL4.

B. Inhibition of IL4 Binding to Receptor

The ability of 3B9 to inhibit the binding of IL4 to its receptor was studied using $^{125}$I-rhIL4 binding to the gibbon cell line, MLA [ATCC TIB201], that bears approximately 6000 receptors per cell. MLA cells were incubated with $^{125}$I-IL4 for 30 minutes at 37° C. Uptake of radioactivity was determined in a gamma counter after separation of cell bound $^{125}$I-IL4 by centrifugation through an oil-gradient. Non-specific binding was determined by incubating in the presence of a 100-fold molar excess of unlabelled IL4 [Park et al, *J. Exp. Med.*, 166:476-488 (1987)]. The IC$_{50}$ value for unlabeled IL4 in this assay was 22 pM when the amount of (added) IL4 was 83 pM. For intact murine (IgG) 3B9 the IC$_{50}$ was 63 pM, and 93 pM for the Fab fragment. At another concentration of IL4 (218 pM), the assay amount for murine (gG) 3B9 was 109 pM.

C. Inhibition of Lymphocyte Proliferation

Using the method described in Spits et al, *J. Immunol.*, 139:1142-1147 (1987), human peripheral blood lymphocytes are incubated for three days with phytohemagglutinin, a T cell mitogen, to upregulate the IL4 receptor. The resultant blast cells are then stimulated for three days further with IL4. Proliferation is measured by the incorporation of $^3$H thymidine. B cell proliferation was measured by the assay of Callard et al, in *Lymphokines and Interferons. A Practical Approach*, Ch. 19, p. 345, modified as follows. Purified human tonsillar B cells are stimulated for 3 days with IL4 and immobilized anti-IgM. Proliferation is measured by the incorporation of $^3$H thymidine.

3B9 (murine) inhibited $^3$H-thymidine incorporation by human peripheral blood T lymphocytes stimulated with 133 pM IL4 and human tonsillar B lymphocytes stimulated by 167 pM IL4. IL2-stimulated T lymphocytes were not affected. The IC$_{50}$ for inhibition of T cell proliferation was 30 pM, and for B cell proliferation 103 pM. The corresponding values for the Fab fragment of 3B9 (murine) were 108 and 393 pM.

D. Inhibition of CD23 Induction

CD23 is the low affinity receptor for IgE (FcERII) and is induced on the membrane of resting B lymphocytes by low concentrations of IL4 as a necessary prerequisite for IgE production. Purified human tonsillar B cells are stimulated for 2 days with IL4. The percentage of cells expressing the CD23 receptor are determined by flow cytometry [Defrance et al, *J. Exp. Med.*, 165:1459-1467 (1987)]. 3B9 (murine) inhibited CD23 expression on human tonsil B lymphocytes stimulated with 8.3 pM IL4 with an IC$_{50}$ value of 136 pM.

E. Inhibition of IgE Secretion

Unlike other assays where IL4 was added at EC$_{50}$ concentrations [Pere et al, *Proc. Natl. Acad. Sci.*, 85:6880-6884 (1988)], IgE secretion was investigated in the presence of concentrations of IL4 giving maximal secretion in order to reduce the variability inherent in this system. T cell proliferation was measured as follows. Human peripheral blood lymphocytes are incubated with IL4 for between 10-18, preferably 12, days. The concentration of IgE in the culture supernatant is determined by ELISA.

IgE secretion was inhibited by 3B9 (murine), and the Fab fragment of 3B9, in the presence of 1.7 nM IL4 giving IC$_{50}$ values of 1.9 and 5.0 nM respectively. The experiment was repeated using a lower concentration of IL4, 667 pM, which reduced the IC$_{50}$ value to 0.65 nM for 3B9 (murine). The molar ratio of antibody (IgG) to IL4 remained unchanged (1:1) over the concentration ranges examined.

F. Summary and Interpretation of Data

The molar ratios of IL4 to various MAbs required for 50% inhibition of function in bioassays is given in Table 2.

TABLE 2

Comparative activity of mAbs 3B9, 6A1 and Humanized 3B9 [IgG1 and IgG4 variants] in IL-4 dependent bioassays

| | IC50 (pM) [range]$_n$ | | | | |
|---|---|---|---|---|---|
| Assay | Murine 3B9 | Murine 3B9 (Fab) | Rat 6A1 | Humanized 3B9 IgG1 | IgG4* |
| RBA | 63 [17-109]$_2$ | 93 | >50000 | | |
| T cell | 30 [10-40]$_4$ | 108 | 87 | 44 [30-56]$_3$ | 40 |
| B cell | 103 [79-120]$_3$ | 393 | 187 | 47 [10-80]$_3$ | 79 |
| CD23 induction | 136 [53-272]$_4$ | 216 | 80 | 333 | |
| IgE synthesis | 658 [370-1070]$_6$ | 1170 | 623 [412-833]$_2$ | 54 [35-83]$_3$ | 406 |

$_n$= number of separte tests carried out.
*The IgG1 and IgG4 variants were assayed at different times.

In all assays, except IgE secretion, IL4 was added at approximate ED$_{50}$ concentrations. The molar ratios of antibody to IL-4 required for 50% inhibition were similar for humanized 3B9, murine 3B9, and 6A 1 in the two lymphocyte proliferation assays, but higher for humanized 3B9 in the CD23 induction assay. The latter is a particularly sensitive assay apparently requiring very low (_5%) receptor occupancy (Kruse et al., *EMBO J*, 12:5121 1993) and, as is evident from the results obtained with murine 3B9, subject to inter assay variation.

A comparison of the activities of rat 6A1 and murine 3B9 demonstrated a similar profile of functional effects, but an unexpected failure of 6A1 to fully inhibit the binding of radioiodinated IL4 to its receptor. The radioiodinated IL4 used in the receptor binding assay is thought to be iodinated at the accessible tyrosine, residue 124. When the ability of 6A1 to inhibit CD23 expression induced by either unlabelled or iodinated IL4 was compared, it was found that inhibition was less efficient against iodinated ligand. These results indicate that 6A1 binds to IL4 in the region of, but not specifically to, tyrosine 124.

Thus on current data, 6A1 is a neutralizing antibody of high affinity, binding to a very different region of IL4 than 3B9.

EXAMPLE 9

Pharmacokinetics

The pharmacokinetics of humanized 3B9 was investigated in the male Sprague Dawley rat. Humanized 3B9 was administered to four animals as an iv bolus dose at 1 mg/kg, blood sampling was continued for 5 weeks post dosing. Plasma humanized 3B9 concentrations were determined using an IL-4/anti-human IgG sandwich ELISA designed to confirm not only the presence of circulating human IgG but also its ability to bind to recombinant human IL-4.

Results from this study are summarized in Table 3.

TABLE 3

Pharmacokinetics of Humanized 3B9 in male Sprague-Dawley Rats (dose: 1 mg/kg iv bolus)

| | Clp (mL/h/kg) |
|---|---|
| Rat 1 | 0.442 |
| Rat 2 | 0.655 |
| Rat 3 | 0.555 |
| Rat 4 | 0.447 |
| Mean | 0.525 |
| SD | 0.101 |

Abbreviation of the pharmacokinetic parameter is as follows: Clp, apparent plasma clearance.

Data indicated that inter-animal variability was relatively small and disappearance of humanized 3B9 from plasma appeared to be biphasic. The apparent plasma clearance was low (0.5 mL/h/kg). The half-life appeared to be 11 days. Thus, the pharmacokinetic characteristics of the CHO cell-derived humanized 3B9 are consistent with other humanized monoclonal antibodies in rats. The long circulating half life of humanized 3B9 in the rat also suggests that when administered to man, humanized 3B9 is likely to be effective over an extended period of time.

Numerous modifications and variations of the present invention are included in the above-identified specification and are expected to be obvious to one of skill in the art. For example, human framework regions or modifications thereof, other than the exemplary antibodies described above, may be used in the construction of humanized antibodies. Such modifications and alterations to the compositions and processes of the present invention are believed to be encompassed in the scope of the claims appended hereto.

What is claimed is:

1. A humanized antibody comprising a heavy chain and a light chain, said antibody characterized by a dissociation constant equal to or less than about $2\times10^{-10}$ M for human IL4, wherein amino acid sequences of the complementarity determining regions for the heavy chain are, in order:

(a) ThrSerGlyMetGlyValSer,         SEQ ID NO:22

(b) HisIleTyrTrpAspAspAspLysArgTyrAsn  SEQ ID NO:24
ProSerLeuLysSer,
and (c) ArgGluThrValPheTyrTrpPheAspVal;  SEQ ID NO:26 and wherein amino acid sequences of the complementarity determining regions for the light chain are, in order:

(a) LysAlaSerGlnSerValAspTyrAspGlyAsp  SEQ ID NO:16
SerTyrMetAsn, (b) AlaAlaSerAsnLeuGluSer,        SEQ ID NO:18
and (c) any one of GlnGlnSerAsnGluAspPro  SEQ ID NO:20
ProThr or GlnGlnSerAsnGluAsp
ProProArg.                                SEQ ID NO:28

2. The antibody according to claim 1 wherein said antibody is optionally linked to an effector agent selected from the group consisting of a non-protein carrier molecule, polystyrene, and plastic beads.

3. A chimeric antibody comprising a heavy chain and a light chain, said antibody characterized by a dissociation constant equal to or less than about $2\times10^{-10}$ M for human IL4, wherein amino acid sequences of the complementarity determining regions for the heavy chain are, in order:

(a) ThrSerGlyMetGlyValSer,         SEQ ID NO:22

(b) HisIleTyrTrpAspAspAspLysArgTyrAsn  SEQ ID NO:24
ProSerLeuLysSer,
and (c) ArgGluThrValPheTyrTrpPheAspVal;  SEQ ID NO:26
and wherein amino acid sequences of the complementarity determining regions for the light chain are, in order:

SEQ ID NO: 16
(a) LysAlaSerGlnSerValAspTyrAspGlyAspSerTyrMetAsn:, (b) AlaAlaSerAsnLeuGluSer:,       SEQ ID NO: 18
and SEQ ID NO: 20
(c) any one of GlnGlnSerAsnGluAspProProThr:
or GlnGlnSerAsnGluAspProProArg:.   SEQ ID NO: 28

4. A composition comprising the antibody of claim 1 and a pharmaceutically acceptable carrier.

5. The antibody according to claim 3 wherein said antibody is optionally linked to an effector agent selected from the group consisting of a non-protein carrier molecule, polystyrene, and plastic beads.

6. A composition comprising the antibody of claim 3 and a pharmaceutically acceptable carrier.

* * * * *

SEQUENCE LISTING (1) GENERAL INFORMATION:

(iii) NUMBER OF SEQUENCES: 58

(2) INFORMATION FOR SEQ ID NO: 1:

(i) SEQUENCE CHARACTERISTICS:
      (A) LENGTH: 396 base pairs
      (B) TYPE: nucleic acid
      (C) STRANDEDNESS: double
      (D) TOPOLOGY: unknown (ii) MOLECULE TYPE: cDNA (ix) FEATURE:
      (A) NAME/KEY: CDS
      (B) LOCATION: 1..396

(xi) SEQUENCE DESCRIPTION: SEQ ID NO: 1:

```
ATG GAG ACA GAC ACA ATC CTG CTA TGG GTG CTG CTG CTC TGG GTT CCA        48
Met Glu Thr Asp Thr Ile Leu Leu Trp Val Leu Leu Leu Trp Val Pro
 1               5                  10                  15

GGC TCC ACT GGT GAC ATT GTG CTG ACC CAA TCT CCA GCT TCT TTG GCT        96
Gly Ser Thr Gly Asp Ile Val Leu Thr Gln Ser Pro Ala Ser Leu Ala
                 20                  25                  30

GTG TCT CTA GGG CAG AGG GCC ACC ATC TCC TGC AAG GCC AGC CAA AGT       144
Val Ser Leu Gly Gln Arg Ala Thr Ile Ser Cys Lys Ala Ser Gln Ser
             35                  40                  45

GTT GAT TAT GAT GGT GAT AGT TAT ATG AAC TGG TAC CAA CAG AAA CCA       192
Val Asp Tyr Asp Gly Asp Ser Tyr Met Asn Trp Tyr Gln Gln Lys Pro
 50                  55                  60

GGA CAG CCA CCC AAA CTC CTC ATC TAT GCT GCA TCC AAT CTA GAA TCT       240
Gly Gln Pro Pro Lys Leu Leu Ile Tyr Ala Ala Ser Asn Leu Glu Ser
 65                  70                  75                  80

GGG ATC CCA GCC AGG TTT AGT GGC AGT GGG TCT GGG ACA GAC TTC ACC       288
Gly Ile Pro Ala Arg Phe Ser Gly Ser Gly Ser Gly Thr Asp Phe Thr
                 85                  90                  95

CTC AAC ATC CAT CCT GTG GAG GAG GAG GAT GCT GCA ACC TAT TAC TGT       336
Leu Asn Ile His Pro Val Glu Glu Glu Asp Ala Ala Thr Tyr Tyr Cys
                100                 105                 110

CAG CAA AGT AAT GAG GAT CCT CCG ACG TTC GGT GGA GGC ACC AAG CTG       384
Gln Gln Ser Asn Glu Asp Pro Pro Thr Phe Gly Gly Gly Thr Lys Leu
```

```
            115                 120                 125
GAA ATC AAA CGG                                                         396
Glu Ile Lys Arg
    130

(2) INFORMATION FOR SEQ ID NO: 2:

(i) SEQUENCE CHARACTERISTICS:
        (A) LENGTH: 132 amino acids
        (B) TYPE: amino acid
        (D) TOPOLOGY: linear (ii) MOLECULE TYPE: protein (xi) SEQUENCE DESCRIPTION: SEQ ID NO: 2:

Met Glu Thr Asp Thr Ile Leu Leu Trp Val Leu Leu Leu Trp Val Pro
 1               5                  10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln Gln Ser Asn Glu Asp Pro Pro Thr Phe Gly Gly Gly Thr Lys Leu
        115                 120                 125

Glu Ile Lys Arg
    130

(2) INFORMATION FOR SEQ ID NO: 3:

(i) SEQUENCE CHARACTERISTICS:
        (A) LENGTH: 483 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 64..483

(xi) SEQUENCE DESCRIPTION: SEQ ID NO: 3:

GAATTCGCGG CCGCTATGCA GGGACAATCA GCAGCAGCAA TGAGGAAGTA AGCCTGTGCA        60

GAT ATG AAC AGG CTT ACT TCC TCA TTG CTG CTG ATT GTC CCT GCA            108
    Met Asn Arg Leu Thr Ser Ser Leu Leu Leu Ile Val Pro Ala
     1               5                  10                  15

TAT GTC CTG TCC CAG GTT ACT CTG AAA GAG TCT GGC CCT GGG ATA TTG        156
Tyr Val Leu Ser Gln Val Thr Leu Lys Glu Ser Gly Pro Gly Ile Leu
                20                  25                  30

CAG CCC TCC CAG ACC CTC AGT CTG ACT TGT TCT TTC TCT GGG TTT TCA        204
Gln Pro Ser Gln Thr Leu Ser Leu Thr Cys Ser Phe Ser Gly Phe Ser
            35                  40                  45

CTG AGC ACT TCT GGT ATG GGT GTG AGC TGG ATT CGT CAG CCT TCA GGA        252
Leu Ser Thr Ser Gly Met Gly Val Ser Trp Ile Arg Gln Pro Ser Gly
        50                  55                  60
```

```
AAG GGT CTG GAG TGG CTG GCA CAC ATT TAC TGG GAT GAT GAC AAG CGC        300
Lys Gly Leu Glu Trp Leu Ala His Ile Tyr Trp Asp Asp Asp Lys Arg
 65              70                  75

TAT AAC CCA TCC CTG AAG AGC CGG CTC ACA ATC TCC AAG GAT ACC TCC        348
Tyr Asn Pro Ser Leu Lys Ser Arg Leu Thr Ile Ser Lys Asp Thr Ser
 80              85                  90                  95

AGC AAC CAG GTA TTC CTC AAG ATC ACC AGT GTG GAC ACT GCA GAT ACT        396
Ser Asn Gln Val Phe Leu Lys Ile Thr Ser Val Asp Thr Ala Asp Thr
                100                 105                 110

GCC ACA TAC TAC TGT GCT CGA AGA GAG ACT GTG TTC TAC TGG TAC TTC        444
Ala Thr Tyr Tyr Cys Ala Arg Arg Glu Thr Val Phe Tyr Trp Tyr Phe
                115                 120                 125

GAT GTC TGG GGC GCA GGG ACC ACG GTC ACC GTC TCC TCA                    483
Asp Val Trp Gly Ala Gly Thr Thr Val Thr Val Ser Ser
                130                 135                 140
```

(2) INFORMATION FOR SEQ ID NO: 4:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Asn Arg Leu Thr Ser Ser Leu Leu Leu Ile Val Pro Ala Tyr
 1               5                  10                  15

Val Leu Ser Gln Val Thr Leu Lys Glu Ser Gly Pro Gly Ile Leu Gln
                20                  25                  30

Pro Ser Gln Thr Leu Ser Leu Thr Cys Ser Phe Ser Gly Phe Ser Leu
                35                  40                  45

Ser Thr Ser Gly Met Gly Val Ser Trp Ile Arg Gln Pro Ser Gly Lys
            50                  55                  60

Gly Leu Glu Trp Leu Ala His Ile Tyr Trp Asp Asp Asp Lys Arg Tyr
 65                 70                  75                  80

Asn Pro Ser Leu Lys Ser Arg Leu Thr Ile Ser Lys Asp Thr Ser Ser
                85                  90                  95

Asn Gln Val Phe Leu Lys Ile Thr Ser Val Asp Thr Ala Asp Thr Ala
                100                 105                 110

Thr Tyr Tyr Cys Ala Arg Arg Glu Thr Val Phe Tyr Trp Tyr Phe Asp
                115                 120                 125

Val Trp Gly Ala Gly Thr Thr Val Thr Val Ser Ser
                130                 135                 140
```

(2) INFORMATION FOR SEQ ID NO: 5:

(i) SEQUENCE CHARACTERISTICS:
        (A) LENGTH: 60 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..60

(xi) SEQUENCE DESCRIPTION: SEQ ID NO: 5:

```
ATG GTG TTG CAG ACC CAG GTC TTC ATT TCT CTG TTG CTC TGG ATC TCT        48
Met Val Leu Gln Thr Gln Val Phe Ile Ser Leu Leu Leu Trp Ile Ser
```

```
                1               5              10              15
GGT GCC TAC GGG                                                                  60
Gly Ala Tyr Gly
            20
```

(2) INFORMATION FOR SEQ ID NO: 6:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Val Leu Gln Thr Gln Val Phe Ile Ser Leu Leu Trp Ile Ser
 1               5                  10                  15
Gly Ala Tyr Gly
            20
```

(2) INFORMATION FOR SEQ ID NO: 7:

(i) SEQUENCE CHARACTERISTICS:
        (A) LENGTH: 57 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 7:

```
ATG GGA TGG AGC TGT ATC ATC CTC TTC TTG GTA GCA ACA GCT ACA GGT    48
Met Gly Trp Ser Cys Ile Ile Leu Phe Leu Val Ala Thr Ala Thr Gly
 1               5                  10                  15
GTC CAC TCC                                                        57
Val His Ser
```

(2) INFORMATION FOR SEQ ID NO: 8:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Gly Trp Ser Cys Ile Ile Leu Phe Leu Val Ala Thr Ala Thr Gly
 1               5                  10                  15
Val His Ser
```

(2) INFORMATION FOR SEQ ID NO: 9:

(i) SEQUENCE CHARACTERISTICS:
        (A) LENGTH: 423 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..423

(xi) SEQUENCE DESCRIPTION: SEQ ID NO: 9:

```
ATG GTG TTG CAG ACC CAG GTC TTC ATT TCT CTG TTG CTC TGG ATC TCT         48
Met Val Leu Gln Thr Gln Val Phe Ile Ser Leu Leu Leu Trp Ile Ser
1               5                   10                  15

GGT GCC TAC GGG CAG GTT ACC CTG AAA GAG TCT GGC CCT GGG ATA TTG         96
Gly Ala Tyr Gly Gln Val Thr Leu Lys Glu Ser Gly Pro Gly Ile Leu
                20                  25                  30

CAG CCC TCC CAG ACC CTC AGT CTG ACT TGT TCT TTC TCT GGG TTT TCA        144
Gln Pro Ser Gln Thr Leu Ser Leu Thr Cys Ser Phe Ser Gly Phe Ser
        35                  40                  45

CTG AGC ACT TCT GGT ATG GGT GTG AGC TGG ATT CGT CAG CCT TCA GGA        192
Leu Ser Thr Ser Gly Met Gly Val Ser Trp Ile Arg Gln Pro Ser Gly
    50                  55                  60

AAG GGT CTG GAG TGG CTG GCA CAC ATT TAC TGG GAT GAT GAC AAG CGC        240
Lys Gly Leu Glu Trp Leu Ala His Ile Tyr Trp Asp Asp Asp Lys Arg
65              70                  75                  80

TAT AAC CCA TCC CTG AAG AGC CGG CTC ACA ATC TCC AAG GAT ACC TCC        288
Tyr Asn Pro Ser Leu Lys Ser Arg Leu Thr Ile Ser Lys Asp Thr Ser
                85                  90                  95

AGC AAC CAG GTA TTC CTC AAG ATC ACC AGT GTG GAC ACT GCA GAT ACT        336
Ser Asn Gln Val Phe Leu Lys Ile Thr Ser Val Asp Thr Ala Asp Thr
            100                 105                 110

GCC ACA TAC TAC TGT GCT CGA AGA GAG ACT GTG TTC TAC TGG TAC TTC        384
Ala Thr Tyr Tyr Cys Ala Arg Arg Glu Thr Val Phe Tyr Trp Tyr Phe
        115                 120                 125

GAT GTC TGG GGC GCA GGG ACC ACG GTC ACC GTC TCC TCA                    423
Asp Val Trp Gly Ala Gly Thr Thr Val Thr Val Ser Ser
130                 135                 140
```

(2) INFORMATION FOR SEQ ID NO: 10:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Val Leu Gln Thr Gln Val Phe Ile Ser Leu Leu Leu Trp Ile Ser
1               5                   10                  15

Gly Ala Tyr Gly Gln Val Thr Leu Lys Glu Ser Gly Pro Gly Ile Leu
                20                  25                  30

Gln Pro Ser Gln Thr Leu Ser Leu Thr Cys Ser Phe Ser Gly Phe Ser
        35                  40                  45

Leu Ser Thr Ser Gly Met Gly Val Ser Trp Ile Arg Gln Pro Ser Gly
    50                  55                  60

Lys Gly Leu Glu Trp Leu Ala His Ile Tyr Trp Asp Asp Asp Lys Arg
65              70                  75                  80

Tyr Asn Pro Ser Leu Lys Ser Arg Leu Thr Ile Ser Lys Asp Thr Ser
                85                  90                  95

Ser Asn Gln Val Phe Leu Lys Ile Thr Ser Val Asp Thr Ala Asp Thr
            100                 105                 110

Ala Thr Tyr Tyr Cys Ala Arg Arg Glu Thr Val Phe Tyr Trp Tyr Phe
        115                 120                 125

Asp Val Trp Gly Ala Gly Thr Thr Val Thr Val Ser Ser
130                 135                 140
```

(2) INFORMATION FOR SEQ ID NO: 11:

(i) SEQUENCE CHARACTERISTICS:
        (A) LENGTH: 423 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..423

(xi) SEQUENCE DESCRIPTION: SEQ ID NO: 11:

```
ATG GTG TTG CAG ACC CAG GTC TTC ATT TCT CTG TTG CTC TGG ATC TCT        48
Met Val Leu Gln Thr Gln Val Phe Ile Ser Leu Leu Leu Trp Ile Ser
 1               5                  10                  15

GGT GCC TAC GGG CAG GTT ACC CTG CGT GAA TCC GGT CCG GCA CTA GTT        96
Gly Ala Tyr Gly Gln Val Thr Leu Arg Glu Ser Gly Pro Ala Leu Val
                 20                  25                  30

AAA CCG ACC CAG ACC CTG ACG TTA ACC TGC ACC TTC TCC GGT TTC TCC       144
Lys Pro Thr Gln Thr Leu Thr Leu Thr Cys Thr Phe Ser Gly Phe Ser
             35                  40                  45

CTG TCG ACC TCC GGT ATG GGT GTT TCC TGG ATC CGT CAG CCG CCG GGT       192
Leu Ser Thr Ser Gly Met Gly Val Ser Trp Ile Arg Gln Pro Pro Gly
         50                  55                  60

AAA GGT CTA GAA TGG CTG GCT CAC ATC TAC TGG GAC GAC GAC AAA CGT       240
Lys Gly Leu Glu Trp Leu Ala His Ile Tyr Trp Asp Asp Asp Lys Arg
 65                  70                  75                  80

TAC AAC CCG AGC CTG AAA TCC CGT CTG ACG ATA TCC AAA GAC ACC TCC       288
Tyr Asn Pro Ser Leu Lys Ser Arg Leu Thr Ile Ser Lys Asp Thr Ser
                 85                  90                  95

CGT AAC CAG GTT GTT CTG ACC ATG ACT AAC ATG GAC CCG GTT GAC ACC       336
Arg Asn Gln Val Val Leu Thr Met Thr Asn Met Asp Pro Val Asp Thr
            100                 105                 110

GCT ACC TAC TAC TGC GCT CGA CGC GAA ACC GTT TTC TAC TGG TAC TTC       384
Ala Thr Tyr Tyr Cys Ala Arg Arg Glu Thr Val Phe Tyr Trp Tyr Phe
        115                 120                 125

GAC GTT TGG GGT CGT GGT ACC CCA GTT ACC GTG AGC TCA                   423
Asp Val Trp Gly Arg Gly Thr Pro Val Thr Val Ser Ser
    130                 135                 140
```

(2) INFORMATION FOR SEQ ID NO: 12:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Val Leu Gln Thr Gln Val Phe Ile Ser Leu Leu Leu Trp Ile Ser
 1               5                  10                  15

Gly Ala Tyr Gly Gln Val Thr Leu Arg Glu Ser Gly Pro Ala Leu Val
                 20                  25                  30

Lys Pro Thr Gln Thr Leu Thr Leu Thr Cys Thr Phe Ser Gly Phe Ser
             35                  40                  45

Leu Ser Thr Ser Gly Met Gly Val Ser Trp Ile Arg Gln Pro Pro Gly
         50                  55                  60

Lys Gly Leu Glu Trp Leu Ala His Ile Tyr Trp Asp Asp Asp Lys Arg
 65                  70                  75                  80
```

```
Tyr Asn Pro Ser Leu Lys Ser Arg Leu Thr Ile Ser Lys Asp Thr Ser
            85                  90                  95

Arg Asn Gln Val Val Leu Thr Met Thr Asn Met Asp Pro Val Asp Thr
                100                 105                 110

Ala Thr Tyr Tyr Cys Ala Arg Arg Glu Thr Val Phe Tyr Trp Tyr Phe
            115                 120                 125

Asp Val Trp Gly Arg Gly Thr Pro Val Thr Val Ser Ser
130                 135                 140
```

(2) INFORMATION FOR SEQ ID NO: 13:

(i) SEQUENCE CHARACTERISTICS:
        (A) LENGTH: 393 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..393

(xi) SEQUENCE DESCRIPTION: SEQ ID NO: 13:

```
ATG GGA TGG AGC TGT ATC ATC CTC TTC TTG GTA GCA ACA GCT ACA GGT      48
Met Gly Trp Ser Cys Ile Ile Leu Phe Leu Val Ala Thr Ala Thr Gly
1               5                   10                  15

GTC CAC TCC GAT ATC GTG ATG ACC CAG TCT CCA GAC TCG CTA GCT GTG      96
Val His Ser Asp Ile Val Met Thr Gln Ser Pro Asp Ser Leu Ala Val
                20                  25                  30

TCT CTG GGC GAG AGG GCC ACC ATC AAC TGC AAG GCC TCC CAA AGT GTT     144
Ser Leu Gly Glu Arg Ala Thr Ile Asn Cys Lys Ala Ser Gln Ser Val
            35                  40                  45

GAT TAT GAT GGT GAT AGT TAT ATG AAC TGG TAT CAG CAG AAA CCC GGG     192
Asp Tyr Asp Gly Asp Ser Tyr Met Asn Trp Tyr Gln Gln Lys Pro Gly
        50                  55                  60

CAG CCT CCT AAG TTG CTC ATT TAC GCT GCA TCC AAT CTA GAA TCT GGG     240
Gln Pro Pro Lys Leu Leu Ile Tyr Ala Ala Ser Asn Leu Glu Ser Gly
65                  70                  75                  80

GTA CCT GAC CGA TTC AGT GGC AGC GGG TCT GGG ACA GAT TTC ACT CTC     288
Val Pro Asp Arg Phe Ser Gly Ser Gly Ser Gly Thr Asp Phe Thr Leu
                85                  90                  95

ACC ATC AGC AGC CTG CAG GCT GAA GAT GTG GCA GTA TAC TAC TGT CAG     336
Thr Ile Ser Ser Leu Gln Ala Glu Asp Val Ala Val Tyr Tyr Cys Gln
                100                 105                 110

CAA AGT AAT GAG GAT CCT CCG AGG TTC GGC GGA GGG ACC AAG GTG GAG     384
Gln Ser Asn Glu Asp Pro Pro Arg Phe Gly Gly Gly Thr Lys Val Glu
            115                 120                 125

ATC AAA CGT                                                          393
Ile Lys Arg
        130
```

(2) INFORMATION FOR SEQ ID NO: 14:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO: 14:

```
Met Gly Trp Ser Cys Ile Ile Leu Phe Leu Val Ala Thr Ala Thr Gly
1               5                   10                  15
```

```
Val His Ser Asp Ile Val Met Thr Gln Ser Pro Asp Ser Leu Ala Val
        20                  25                  30

Ser Leu Gly Glu Arg Ala Thr Ile Asn Cys Lys Ala Ser Gln Ser Val
    35                  40                  45

Asp Tyr Asp Gly Asp Ser Tyr Met Asn Trp Tyr Gln Gln Lys Pro Gly
50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
                100                 105                 110

Gln Ser Asn Glu Asp Pro Pro Arg Phe Gly Gly Gly Thr Lys Val Glu
            115                 120                 125

Ile Lys Arg
    130
```

(2) INFORMATION FOR SEQ ID NO: 15:

(i) SEQUENCE CHARACTERISTICS:
        (A) LENGTH: 45 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..45

(xi) SEQUENCE DESCRIPTION: SEQ ID NO: 15:

```
AAG GCC AGC CAA AGT GTT GAT TAT GAT GGT GAT AGT TAT ATG AAC      45
Lys Ala Ser Gln Ser Val Asp Tyr Asp Gly Asp Ser Tyr Met Asn
1               5                   10                  15
```

(2) INFORMATION FOR SEQ ID NO: 16:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO: 16:

```
Lys Ala Ser Gln Ser Val Asp Tyr Asp Gly Asp Ser Tyr Met Asn
1               5                   10                  15
```

(2) INFORMATION FOR SEQ ID NO: 17:

(i) SEQUENCE CHARACTERISTICS:
        (A) LENGTH: 21 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..21

(xi) SEQUENCE DESCRIPTION: SEQ ID NO: 17:

```
GCT GCA TCC AAT CTA GAA TCT                                       21
```

```
Ala Ala Ser Asn Leu Glu Ser
  1               5

(2) INFORMATION FOR SEQ ID NO: 18:

(i) SEQUENCE CHARACTERISTICS:
         (A) LENGTH: 7 amino acids
         (B) TYPE: amino acid
         (D) TOPOLOGY: linear (ii) MOLECULE TYPE: protein (xi) SEQUENCE DESCRIPTION: SEQ ID NO: 18:

Ala Ala Ser Asn Leu Glu Ser
  1               5

(2) INFORMATION FOR SEQ ID NO: 19:

(i) SEQUENCE CHARACTERISTICS:
         (A) LENGTH: 27 base pairs
         (B) TYPE: nucleic acid
         (C) STRANDEDNESS: double
         (D) TOPOLOGY: unknown (ii) MOLECULE TYPE: cDNA (ix) FEATURE:
         (A) NAME/KEY: CDS
         (B) LOCATION: 1..27

(xi) SEQUENCE DESCRIPTION: SEQ ID NO: 19:

CAG CAA AGT AAT GAG GAT CCT CCG ACG                         27
Gln Gln Ser Asn Glu Asp Pro Pro Thr
  1               5

(2) INFORMATION FOR SEQ ID NO: 20:

(i) SEQUENCE CHARACTERISTICS:
         (A) LENGTH: 9 amino acids
         (B) TYPE: amino acid
         (D) TOPOLOGY: linear (ii) MOLECULE TYPE: protein (xi) SEQUENCE DESCRIPTION: SEQ ID NO: 20:

Gln Gln Ser Asn Glu Asp Pro Pro Thr
  1               5

(2) INFORMATION FOR SEQ ID NO: 21:

(i) SEQUENCE CHARACTERISTICS:
         (A) LENGTH: 21 base pairs
         (B) TYPE: nucleic acid
         (C) STRANDEDNESS: double
         (D) TOPOLOGY: unknown (ii) MOLECULE TYPE: cDNA (ix) FEATURE:
         (A) NAME/KEY: CDS
         (B) LOCATION: 1..21

(xi) SEQUENCE DESCRIPTION: SEQ ID NO: 21:

ACT TCT GGT ATG GGT GTG AGC                                 21
Thr Ser Gly Met Gly Val Ser
  1               5

(2) INFORMATION FOR SEQ ID NO: 22:

(i) SEQUENCE CHARACTERISTICS:
```

(A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 22:

Thr Ser Gly Met Gly Val Ser
 1               5

(2) INFORMATION FOR SEQ ID NO: 23:

(i) SEQUENCE CHARACTERISTICS:
        (A) LENGTH: 48 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..48

(xi) SEQUENCE DESCRIPTION: SEQ ID NO: 23:

CAC ATT TAC TGG GAT GAT GAC AAG CGC TAT AAC CCA TCC CTG AAG AGC      48
His Ile Tyr Trp Asp Asp Asp Lys Arg Tyr Asn Pro Ser Leu Lys Ser
 1               5                  10                  15

(2) INFORMATION FOR SEQ ID NO: 24:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 24:

His Ile Tyr Trp Asp Asp Asp Lys Arg Tyr Asn Pro Ser Leu Lys Ser
 1               5                  10                  15

(2) INFORMATION FOR SEQ ID NO: 25:

(i) SEQUENCE CHARACTERISTICS:
        (A) LENGTH: 33 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..33

(xi) SEQUENCE DESCRIPTION: SEQ ID NO: 25:

AGA GAG ACT GTG TTC TAC TGG TAC TTC GAT GTC      33
Arg Glu Thr Val Phe Tyr Trp Tyr Phe Asp Val
 1               5                  10

(2) INFORMATION FOR SEQ ID NO: 26:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 26:

```
Arg Glu Thr Val Phe Tyr Trp Tyr Phe Asp Val
 1               5                  10
```

(2) INFORMATION FOR SEQ ID NO: 27:

(i) SEQUENCE CHARACTERISTICS:
        (A) LENGTH: 27 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..27

(xi) SEQUENCE DESCRIPTION: SEQ ID NO: 27:

```
CAG CAA AGT AAT GAG GAT CCT CCG AGG                          27
Gln Gln Ser Asn Glu Asp Pro Pro Arg
 1               5
```

(2) INFORMATION FOR SEQ ID NO: 28:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 28:

```
Gln Gln Ser Asn Glu Asp Pro Pro Arg
 1               5
```

(2) INFORMATION FOR SEQ ID NO: 29:

(i) SEQUENCE CHARACTERISTICS:
        (A) LENGTH: 36 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 29:

```
CTAACACTCA TTCCTGTTGA AGCTCTTGAC AATGGG                      36
```

(2) INFORMATION FOR SEQ ID NO: 30:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 30:

```
GTACATATGC AAGGCTTACA ACCACAATC                              29
```

(2) INFORMATION FOR SEQ ID NO: 31:

(i) SEQUENCE CHARACTERISTICS:
        (A) LENGTH: 117 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 31:

```
GGTTACCCTG CGTGAATCCG GTCCGGCACT AGTTAAACCG ACCCAGACCC TGACGTTAAC      60
CTGCACCTTC TCCGGTTTCT CCCTGTCGAC CTCCGGTATG GGTGTTTCCT GGATCCG        117
```

(2) INFORMATION FOR SEQ ID NO: 32:

(i) SEQUENCE CHARACTERISTICS:
        (A) LENGTH: 120 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 32:

```
TCAGCCGCCG GGTAAAGGTC TAGAATGGCT GGCTCACATC TACTGGGACG ACGACAAACG      60
TTACAACCCG AGCCTGAAAT CCCGTCTGAC GATATCCAAA GACACCTCCC GTAACCAGGT     120
```

(2) INFORMATION FOR SEQ ID NO: 33:

(i) SEQUENCE CHARACTERISTICS:
        (A) LENGTH: 120 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 33:

```
TGTTCTGACC ATGGACCCGG TTGACACCGC TACCTACTAC TGCGCTCGTC GCGAAACCGT      60
TTTCTACTGG TACTTCGACG TTTGGGGTCG TGGTACCCCA GTTACCGTGA GCTCCCAACC     120
```

(2) INFORMATION FOR SEQ ID NO: 34:

(i) SEQUENCE CHARACTERISTICS:
        (A) LENGTH: 25 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 34:

```
ACCCGGCGGC TGACGGATCC AGGAA                                            25
```

(2) INFORMATION FOR SEQ ID NO: 35:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 35:

```
ATGGTCAGAA CAACCTGGTT ACGG                                             24
```

(2) INFORMATION FOR SEQ ID NO: 36:

(i) SEQUENCE CHARACTERISTICS:
        (A) LENGTH: 25 base pairs
        (B) TYPE: nucleic acid
        (C) STRANDEDNESS: single -continued (D) TOPOLOGY: unknown (ii) MOLECULE TYPE: DNA (genomic)

(xi) SEQUENCE DESCRIPTION: SEQ ID NO: 36:

TTCGGGTTAC CCTGCGTGAA TCCGG                                             25

(2) INFORMATION FOR SEQ ID NO: 37:

(i) SEQUENCE CHARACTERISTICS:
            (A) LENGTH: 21 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO: 37:

CCAACCCTCG AGTGCCATTG A                                                 21

(2) INFORMATION FOR SEQ ID NO: 38:

(i) SEQUENCE CHARACTERISTICS:
            (A) LENGTH: 43 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO: 38:

CTAGCTGTGT CTCTGGGCGA GAGGGCCACC ATCAACTGCA AGG                         43

(2) INFORMATION FOR SEQ ID NO: 39:

(i) SEQUENCE CHARACTERISTICS:
            (A) LENGTH: 39 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO: 39:

CCTTGCAGTT GATGGTGGCC CTCTCGCCCA GAGACACAG                              39

(2) INFORMATION FOR SEQ ID NO: 40:

(i) SEQUENCE CHARACTERISTICS:
            (A) LENGTH: 67 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO: 40:

TCGAGAGGCC TCCCAAAGTG TTGATTATGA TGGTGATAGT TATATGAACT GGTATCAGCA       60

GAAACCC                                                                 67

(2) INFORMATION FOR SEQ ID NO: 41:

(i) SEQUENCE CHARACTERISTICS:
            (A) LENGTH: 63 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO: 41:

GGGTTTCTGC TGATACCAGT TCATATAACT ATCACCATCA TAATCAACAC TTTGGGAGGC     60

CTC                                                                 63

(2) INFORMATION FOR SEQ ID NO: 42:

(i) SEQUENCE CHARACTERISTICS:
          (A) LENGTH: 51 base pairs
          (B) TYPE: nucleic acid
          (C) STRANDEDNESS: single
          (D) TOPOLOGY: unknown (ii) MOLECULE TYPE: DNA (genomic)

(xi) SEQUENCE DESCRIPTION: SEQ ID NO: 42:

ATACTACTGT CAGCAAAGTA ATGAGGATCC TCCGAGGTTC GGCGGAGGGA C             51

(2) INFORMATION FOR SEQ ID NO: 43:

(i) SEQUENCE CHARACTERISTICS:
          (A) LENGTH: 53 base pairs
          (B) TYPE: nucleic acid
          (C) STRANDEDNESS: single
          (D) TOPOLOGY: unknown (ii) MOLECULE TYPE: DNA (genomic)

(xi) SEQUENCE DESCRIPTION: SEQ ID NO: 43:

CTTGGTCCCT CCGCCGAACC TCGGAGGATC CTCATTACTT TGCTGACAGT AGT           53

(2) INFORMATION FOR SEQ ID NO: 44:

(i) SEQUENCE CHARACTERISTICS:
          (A) LENGTH: 55 base pairs
          (B) TYPE: nucleic acid
          (C) STRANDEDNESS: single
          (D) TOPOLOGY: unknown (ii) MOLECULE TYPE: DNA (genomic)

(xi) SEQUENCE DESCRIPTION: SEQ ID NO: 44:

GGGCAGCCTC CTAAGTTGCT CATTTACGCT GCATCCAATC TAGAATCTGG GGTAC         55

(2) INFORMATION FOR SEQ ID NO: 45:

(i) SEQUENCE CHARACTERISTICS:
          (A) LENGTH: 51 base pairs
          (B) TYPE: nucleic acid
          (C) STRANDEDNESS: single
          (D) TOPOLOGY: unknown (ii) MOLECULE TYPE: DNA (genomic)

(xi) SEQUENCE DESCRIPTION: SEQ ID NO: 45:

CCCAGATTCT AGATTGGATG CAGCGTAAAT GAGCAACTTA GGAGGCTGCC C             51

(2) INFORMATION FOR SEQ ID NO: 46:

(i) SEQUENCE CHARACTERISTICS:
          (A) LENGTH: 83 base pairs
          (B) TYPE: nucleic acid
          (C) STRANDEDNESS: single
          (D) TOPOLOGY: unknown (ii) MOLECULE TYPE: DNA (genomic)

(xi) SEQUENCE DESCRIPTION: SEQ ID NO: 46:

AATTCGAGGA CGCCAGCAAC ATGGTGTTGC AGACCCAGGT CTTCATTTCT CTGTTGCTCT        60

GGATCTCTGG TGCCTACGGG CAG        83

(2) INFORMATION FOR SEQ ID NO: 47:

(i) SEQUENCE CHARACTERISTICS:
        (A) LENGTH: 84 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 47:

GTAACCTGCC CGTAGGCACC AGAGATCCAG AGCAACAGAG AAATGAAGAC CTGGGTCTGC        60

AACACCATGT TGCTGGCGTC CTCG        84

(2) INFORMATION FOR SEQ ID NO: 48:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 48:

CAGGTTACCC TGAAAGAGTC        20

(2) INFORMATION FOR SEQ ID NO: 49:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 49:

GAAGTAGTCC TTGACCAG        18

(2) INFORMATION FOR SEQ ID NO: 50:

(i) SEQUENCE CHARACTERISTICS:
        (A) LENGTH: 31 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 50:

GTCACCGTCT CCTCAGCTAG CACCAAGGGG C        31

(2) INFORMATION FOR SEQ ID NO: 51:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: DNA (genomic)

-continued

```
    (xi) SEQUENCE DESCRIPTION: SEQ ID NO: 51:

CTTGGTGCTA GCTGAGGAGA CG                                              22

(2) INFORMATION FOR SEQ ID NO: 52:

(i) SEQUENCE CHARACTERISTICS:
         (A) LENGTH: 47 base pairs
         (B) TYPE: nucleic acid
         (C) STRANDEDNESS: single
         (D) TOPOLOGY: unknown (ii) MOLECULE TYPE: DNA (genomic)

(xi) SEQUENCE DESCRIPTION: SEQ ID NO: 52:

CATCTAGATG GCGCCGCCAC AGTACGTTTG ATCTCCAGCT TGGTCCC                   47

(2) INFORMATION FOR SEQ ID NO: 53:

(i) SEQUENCE CHARACTERISTICS:
         (A) LENGTH: 45 base pairs
         (B) TYPE: nucleic acid
         (C) STRANDEDNESS: double
         (D) TOPOLOGY: unknown (ii) MOLECULE TYPE: cDNA (xi) SEQUENCE DESCRIPTION: SEQ ID NO: 53:

AAGGCCTCCC AAAGTGTTGA TTATGATGGT GATAGTTATA TGAAC                     45

(2) INFORMATION FOR SEQ ID NO: 54:

(i) SEQUENCE CHARACTERISTICS:
         (A) LENGTH: 21 base pairs
         (B) TYPE: nucleic acid
         (C) STRANDEDNESS: double
         (D) TOPOLOGY: unknown (ii) MOLECULE TYPE: cDNA (xi) SEQUENCE DESCRIPTION: SEQ ID NO: 54:

ACCTCCGGTA TGGGTGTTTC C                                               21

(2) INFORMATION FOR SEQ ID NO: 55:

(i) SEQUENCE CHARACTERISTICS:
         (A) LENGTH: 48 base pairs
         (B) TYPE: nucleic acid
         (C) STRANDEDNESS: double
         (D) TOPOLOGY: unknown (ii) MOLECULE TYPE: cDNA (xi) SEQUENCE DESCRIPTION: SEQ ID NO: 55:

CACATCTACT GGGACGACGA CAAACGTTAC AACCCGAGCC TGAAATCC                  48

(2) INFORMATION FOR SEQ ID NO: 56:

(i) SEQUENCE CHARACTERISTICS:
         (A) LENGTH: 33 base pairs
         (B) TYPE: nucleic acid
         (C) STRANDEDNESS: double
         (D) TOPOLOGY: unknown (ii) MOLECULE TYPE: cDNA (xi) SEQUENCE DESCRIPTION: SEQ ID NO: 56:

CGCGAAACCG TTTTCTACTG GTACTTCGAC GTT                                  33
```

(2) INFORMATION FOR SEQ ID NO: 57:

(i) SEQUENCE CHARACTERISTICS:
        (A) LENGTH: 393 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..393

(xi) SEQUENCE DESCRIPTION: SEQ ID NO: 57:

```
ATG GGA TGG AGC TGT ATC ATC CTC TTC TTG GTA GCA ACA GCT ACA GGT        48
Met Gly Trp Ser Cys Ile Ile Leu Phe Leu Val Ala Thr Ala Thr Gly
 1               5                  10                  15

GTC CAC TCC GAT ATC GTG ATG ACC CAG TCT CCA GAC TCG CTA GCT GTG        96
Val His Ser Asp Ile Val Met Thr Gln Ser Pro Asp Ser Leu Ala Val
             20                  25                  30

TCT CTG GGC GAG AGG GCC ACC ATC AAC TGC AAG GCC TCC CAA AGT GTT       144
Ser Leu Gly Glu Arg Ala Thr Ile Asn Cys Lys Ala Ser Gln Ser Val
         35                  40                  45

GAT TAT GAT GGT GAT AGT TAT ATG AAC TGG TAT CAG CAG AAA CCC GGG       192
Asp Tyr Asp Gly Asp Ser Tyr Met Asn Trp Tyr Gln Gln Lys Pro Gly
     50                  55                  60

CAG CCT CCT AAG TTG CTC ATT TAC GCT GCA TCC AAT CTA GAA TCT GGG       240
Gln Pro Pro Lys Leu Leu Ile Tyr Ala Ala Ser Asn Leu Glu Ser Gly
 65                  70                  75                  80

GTA CCT GAC CGA TTC AGT GGC AGC GGG TCT GGG ACA GAT TTC ACT CTC       288
Val Pro Asp Arg Phe Ser Gly Ser Gly Ser Gly Thr Asp Phe Thr Leu
                 85                  90                  95

ACC ATC AGC AGC CTG CAG GCT GAA GAT GTG GCA GTA TAC TAC TGT CAG       336
Thr Ile Ser Ser Leu Gln Ala Glu Asp Val Ala Val Tyr Tyr Cys Gln
            100                 105                 110

CAA AGT AAT GAG GAT CCT CCG ACG TTC GGC GGA GGG ACC AAA GTG GAG       384
Gln Ser Asn Glu Asp Pro Pro Thr Phe Gly Gly Gly Thr Lys Val Glu
        115                 120                 125

ATC AAA CGT                                                           393
Ile Lys Arg
    130
```

(2) INFORMATION FOR SEQ ID NO: 58:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO: 58:

```
Met Gly Trp Ser Cys Ile Ile Leu Phe Leu Val Ala Thr Ala Thr Gly
 1               5                  10                  15

Val His Ser Asp Ile Val Met Thr Gln Ser Pro Asp Ser Leu Ala Val
             20                  25                  30

Ser Leu Gly Glu Arg Ala Thr Ile Asn Cys Lys Ala Ser Gln Ser Val
         35                  40                  45

Asp Tyr Asp Gly Asp Ser Tyr Met Asn Trp Tyr Gln Gln Lys Pro Gly
     50                  55                  60

Gln Pro Pro Lys Leu Leu Ile Tyr Ala Ala Ser Asn Leu Glu Ser Gly
 65                  70                  75                  80
```

-continued

```
Val Pro Asp Arg Phe Ser Gly Ser Gly Ser Gly Thr Asp Phe Thr Leu
            85                  90                  95

Thr Ile Ser Ser Leu Gln Ala Glu Asp Val Ala Val Tyr Tyr Cys Gln
            100                 105                 110

Gln Ser Asn Glu Asp Pro Pro Thr Phe Gly Gly Gly Thr Lys Val Glu
            115                 120                 125

Ile Lys Arg
     130
```